(12) United States Patent
Draaisma et al.

(10) Patent No.: US 9,873,765 B2
(45) Date of Patent: *Jan. 23, 2018

(54) BIODEGRADABLE POLYESTERAMIDE COPOLYMERS FOR DRUG DELIVERY

(71) Applicant: DSM IP ASSETS B.V., Heerlen (NL)

(72) Inventors: Guy Draaisma, Echt (NL); George Mihov, Echt (NL)

(73) Assignee: DSM IP ASSETS, B.V., Heerlen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 15/252,350

(22) Filed: Aug. 31, 2016

(65) Prior Publication Data

US 2017/0051110 A1  Feb. 23, 2017

Related U.S. Application Data

(62) Division of application No. 14/128,839, filed as application No. PCT/EP2012/062265 on Jun. 25, 2012.

(30) Foreign Application Priority Data

Jun. 23, 2011 (EP) ...................................... 11171191

(51) Int. Cl.
  C08G 69/44 (2006.01)
  C08L 77/12 (2006.01)
  (Continued)

(52) U.S. Cl.
  CPC ............ C08G 69/44 (2013.01); A61K 9/7007 (2013.01); A61K 31/165 (2013.01); A61K 47/34 (2013.01);
  (Continued)

(58) Field of Classification Search
  None
  See application file for complete search history.

(56) References Cited

U.S. PATENT DOCUMENTS 4,129,594 A  12/1978 Baker et al.
4,221,787 A   9/1980 Bodor et al.
(Continued)

FOREIGN PATENT DOCUMENTS

AU  2001287015  3/2002
AU  2006204654  9/2006
(Continued)

OTHER PUBLICATIONS (Algebraic Properties [Axioms], p. 1, 2009 Mathematics Standards of Learning, Virginia Department of Education, Fall 2012; accessed as http://www.doe.virginia.gov/instruction/mathematics/resources/va_algebraic_properties.pdf, on Aug. 7, 2017).*
(Continued)

Primary Examiner — Bethany P Barham
Assistant Examiner — Dominic Lazaro
(74) Attorney, Agent, or Firm — Kevin M. Bull

(57) ABSTRACT

The present invention relates to a poly (ester amide) (PEA) having a chemical formula described by structural formula (IV), Formula (IV)

(Continued)

-continued

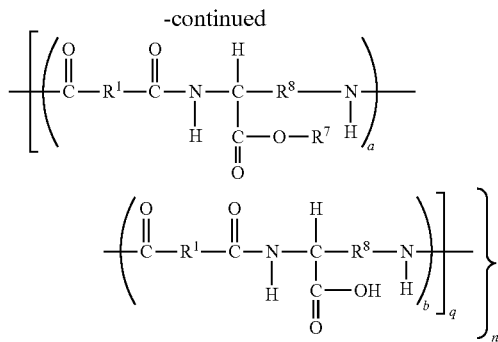

wherein
  m+p varies from 0.9-0.1 and q varies from 0.1 to 0.9
  m+p+q=1 whereby m or p could be 0
  n is about 5 to about 300; (pref. 50-200)
  $R_1$ is independently selected from the group consisting of $(C_2-C_{20})$ alkylene, $(C_2-C_{20})$ alkenylene, —$(R_9$—CO—O—$R_{10}$—O—CO—$R_9)$—, —$CHR_{11}$—O—CO—$R_{12}$—COOC$R_{11}$— and combinations thereof;
  $R_3$ and $R_4$ in a single backbone unit m or p, respectively, are independently selected from the group consisting of hydrogen, $(C_1-C_6)$alkyl, $(C_2-C_6)$alkenyl, $(C_2-C_6)$alkynyl, $(C_6-C_{10})$aryl, $(C_1-C_6)$alkyl, —$(CH_2)SH$, —$(CH_2)_2S(CH_3)$, —$CH_2OH$, —$CH(OH)CH_3$, —$(CH_2)_4NH_3+$, —$(CH_2)_3NHC(=NH_2+)NH_2$, —$CH_2COOH$, —$(CH_2)COOH$, —$CH_2$—CO—$NH_2$, —$CH_2CH_2$—CO—$NH_2$, —$CH_2CH_2COOH$, $CH_3$—$CH_2$—$CH(CH_3)$—, $(CH_3)_2$—CH—$CH_2$—, $H_2N$—$(CH_2)_4$—, $Ph-CH_2$—, $CH=C$—$CH_2$—, $HO-p-Ph-CH_2$—, $(CH_3)_2$—CH—, $Ph-NH$—, $NH$—$(CH_2)_3$—C—, $NH$—$CH=N$—$CH=C$—$CH_2$—.
  $R_5$ is selected from the group consisting of $(C_2-C_{20})$ alkylene, $(C_2-C_{20})$alkenylene, alkyloxy or oligoethyleneglycol
  $R_6$ is selected from bicyclic-fragments of 1,4:3,6-dianhydrohexitols of structural formula (III);

Formula III

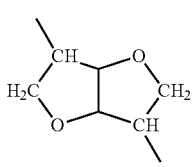

$R_7$ is selected from the group consisting of $(C_6-C_{10})$aryl $(C_1-C_6)$alkyl
  $R_8$ is —$(CH2)4$-;
  $R_9$ or $R_{10}$ are independently selected from $C_2-C_{12}$ alkylene or $C_2-C_{12}$ alkenylene.
  $R_{11}$ or $R_{12}$ are independently selected from H, methyl, $C_2-C_{12}$ alkylene or $C_2-C_{12}$ alkenylene whereby a is at least 0.05 and b is at least 0.05 and a+b=1.

36 Claims, 7 Drawing Sheets

(51) Int. Cl.
  A61K 31/165 (2006.01)
  C09D 177/12 (2006.01)
  A61K 47/34 (2017.01)
  A61K 9/70 (2006.01)
(52) U.S. Cl.
  CPC ............ *C08L 77/12* (2013.01); *C09D 177/12* (2013.01); *C08L 2203/16* (2013.01); *C08L 2205/025* (2013.01)

(56) References Cited

U.S. PATENT DOCUMENTS

| | | | |
|---|---|---|---|
| 4,443,563 A | 4/1984 | Dirlikov et al. |
| 4,550,730 A | 11/1985 | Shalaby et al. |
| 4,994,551 A | 2/1991 | Fung et al. |
| 5,057,313 A | 10/1991 | Shih et al. |
| 5,091,560 A | 2/1992 | Rowland |
| 5,100,992 A | 3/1992 | Cohn et al. |
| 5,133,742 A | 7/1992 | Pinchuk |
| 5,206,341 A | 4/1993 | Ibay et al. |
| 5,286,837 A | 2/1994 | Barrows et al. |
| 5,300,114 A | 4/1994 | Gwon et al. |
| 5,449,513 A | 9/1995 | Yokoyama et al. |
| 5,482,700 A | 1/1996 | Deutsch et al. |
| 5,485,496 A | 1/1996 | Lee et al. |
| 5,514,379 A | 5/1996 | Weissleder et al. |
| 5,516,881 A | 5/1996 | Lee et al. |
| 5,554,692 A | 9/1996 | Ross |
| 5,583,206 A | 12/1996 | Snow et al. |
| 5,591,227 A | 1/1997 | Dinh et al. |
| 5,610,241 A | 3/1997 | Lee et al. |
| 5,653,998 A | 8/1997 | Hamann et al. |
| 5,721,131 A | 2/1998 | Rudolph et al. |
| 5,753,234 A | 5/1998 | Lee et al. |
| 5,762,939 A | 6/1998 | Smith et al. |
| 5,770,229 A | 6/1998 | Tanihara et al. |
| 5,849,841 A | 12/1998 | Muhlebach et al. |
| 5,852,155 A | 12/1998 | Bussink et al. |
| 5,858,368 A | 1/1999 | Smith et al. |
| 5,861,387 A | 1/1999 | Labrie et al. |
| 5,874,064 A | 2/1999 | Edwards et al. |
| 5,882,679 A | 3/1999 | Needham |
| 5,885,491 A | 3/1999 | Galan Valdivia et al. |
| 5,904,936 A | 5/1999 | Huille et al. |
| 5,906,934 A | 5/1999 | Grande et al. |
| 5,916,585 A | 6/1999 | Cook et al. |
| 5,919,893 A | 7/1999 | Roby et al. |
| 5,929,893 A | 7/1999 | Son et al. |
| 5,968,794 A | 10/1999 | Samain et al. |
| 5,972,027 A | 10/1999 | Johnson |
| 6,004,573 A | 12/1999 | Rathi et al. |
| 6,103,526 A | 8/2000 | Smith et al. |
| 6,111,058 A | 8/2000 | Warzelhan et al. |
| 6,153,252 A | 11/2000 | Hossainy et al. |
| 6,171,610 B1 | 1/2001 | Vacanti et al. |
| 6,210,441 B1 | 4/2001 | Flodin |
| 6,221,997 B1 | 4/2001 | Woodhouse et al. |
| 6,228,391 B1 | 5/2001 | Shimizu et al. |
| 6,245,532 B1 | 6/2001 | Smith et al. |
| 6,299,597 B1 | 10/2001 | Buscemi et al. |
| 6,342,300 B1 | 1/2002 | Bengs et al. |
| 6,352,667 B1 | 3/2002 | English |
| 6,365,160 B1 | 4/2002 | Webb et al. |
| 6,428,807 B1 | 8/2002 | MacFarlan et al. |
| 6,476,204 B1 | 11/2002 | Kim et al. |
| 6,503,538 B1 | 1/2003 | Chu et al. |
| 6,521,431 B1 | 2/2003 | Kiser et al. |
| 6,541,606 B2 | 4/2003 | Margolin et al. |
| 6,660,525 B2 | 12/2003 | Martin et al. |
| 6,703,040 B2 | 3/2004 | Katsarava et al. |
| 6,716,445 B2 | 4/2004 | Won et al. |
| 6,793,938 B2 | 9/2004 | Sankaram |
| 6,830,747 B2 | 12/2004 | Lang et al. |
| 6,982,249 B1 | 1/2006 | Schmaier et al. |
| 6,984,393 B2 | 1/2006 | Amsden |
| 6,994,867 B1 | 2/2006 | Hossainy et al. |
| 7,026,156 B1 | 4/2006 | Clark et al. |
| 7,041,785 B1 | 5/2006 | Recoli et al. |
| 7,122,202 B2 | 10/2006 | Allen et al. |

(56) References Cited

U.S. PATENT DOCUMENTS

| | | |
|---|---|---|
| 7,220,816 B2 | 5/2007 | Pacetti et al. |
| 7,304,122 B2 | 12/2007 | Chu et al. |
| 7,408,018 B2 | 8/2008 | Chu et al. |
| 7,538,180 B2 | 5/2009 | Pacetti et al. |
| 7,649,022 B2 | 1/2010 | Gomurashvili et al. |
| 7,658,727 B1 | 2/2010 | Fernandes et al. |
| 7,670,829 B2 | 3/2010 | Spagnoli et al. |
| 7,744,861 B2 | 6/2010 | Zhao et al. |
| 7,785,618 B2 | 8/2010 | Elmaleh et al. |
| 7,794,494 B2 | 9/2010 | Sahatjian et al. |
| 7,794,706 B2 | 9/2010 | Carpenter et al. |
| 7,863,406 B2 | 1/2011 | Chu et al. |
| 7,935,493 B2 | 5/2011 | Michnick et al. |
| 8,067,031 B2 | 11/2011 | Daniloff et al. |
| 8,163,269 B2 | 4/2012 | Carpenter et al. |
| 2001/0038851 A1 | 11/2001 | Allen et al. |
| 2002/0015720 A1 | 2/2002 | Katsarava et al. |
| 2002/0034532 A1 | 3/2002 | Brodbeck et al. |
| 2002/0044972 A1 | 4/2002 | Davis et al. |
| 2002/0049495 A1 | 4/2002 | Kutryk et al. |
| 2002/0106369 A1 | 8/2002 | Horvath et al. |
| 2002/0147296 A1 | 10/2002 | Teller et al. |
| 2002/0164374 A1 | 11/2002 | Jackson et al. |
| 2002/0165347 A1 | 11/2002 | Fox et al. |
| 2002/0168338 A1 | 11/2002 | Baird |
| 2002/0173586 A1 | 11/2002 | Jeong et al. |
| 2003/0064053 A1 | 4/2003 | Liu et al. |
| 2003/0130185 A1 | 7/2003 | Bar-Or et al. |
| 2003/0175239 A1 | 9/2003 | Margolin et al. |
| 2003/0215454 A1 | 11/2003 | Colb et al. |
| 2003/0217748 A1 | 11/2003 | Giroux |
| 2003/0229393 A1 | 12/2003 | Kutryk et al. |
| 2004/0007958 A1 | 1/2004 | Lim et al. |
| 2004/0017387 A1 | 1/2004 | Soltero et al. |
| 2004/0024069 A1 | 2/2004 | Chen et al. |
| 2004/0057958 A1 | 3/2004 | Waggoner, Jr. et al. |
| 2004/0063606 A1 | 4/2004 | Chu et al. |
| 2004/0110285 A1 | 6/2004 | Lendlein et al. |
| 2004/0170685 A1 | 9/2004 | Carpenter et al. |
| 2004/0213759 A1 | 10/2004 | Zalipsky et al. |
| 2004/0213766 A1 | 10/2004 | Francois |
| 2004/0253293 A1 | 12/2004 | Shafiee et al. |
| 2004/0254151 A1 | 12/2004 | Ralston et al. |
| 2004/0258702 A1 | 12/2004 | Blonder et al. |
| 2005/0004378 A1 | 1/2005 | Mane et al. |
| 2005/0013812 A1 | 1/2005 | Dow et al. |
| 2005/0019366 A1 | 1/2005 | Zeldis |
| 2005/0019404 A1 | 1/2005 | Sung et al. |
| 2005/0025752 A1 | 2/2005 | Kutryk et al. |
| 2005/0043787 A1 | 2/2005 | Kutryk et al. |
| 2005/0053667 A1 | 3/2005 | Irvine et al. |
| 2005/0064602 A1 | 3/2005 | Kaufman et al. |
| 2005/0138689 A1 | 6/2005 | Aukerman |
| 2005/0169968 A1 | 8/2005 | Elmaleh et al. |
| 2005/0175583 A1 | 8/2005 | Tamarkin et al. |
| 2005/0208091 A1 | 9/2005 | Pacetti |
| 2005/0216074 A1 | 9/2005 | Sahatjian et al. |
| 2005/0238689 A1 | 10/2005 | Carpenter et al. |
| 2005/0245637 A1 | 11/2005 | Hossainy et al. |
| 2005/0260259 A1 | 11/2005 | Bolotin |
| 2005/0265960 A1 | 12/2005 | Pacetti et al. |
| 2005/0271700 A1 | 12/2005 | DesNoyer et al. |
| 2005/0271701 A1 | 12/2005 | Cottone, Jr. et al. |
| 2005/0287184 A1 | 12/2005 | Hossainy et al. |
| 2005/0288481 A1 | 12/2005 | DesNoyer et al. |
| 2006/0002947 A1 | 1/2006 | Humphreys et al. |
| 2006/0008532 A1 | 1/2006 | Govardhan et al. |
| 2006/0009498 A1 | 1/2006 | Whitcup |
| 2006/0013855 A1 | 1/2006 | Carpenter et al. |
| 2006/0024357 A1 | 2/2006 | Carpenter et al. |
| 2006/0036311 A1 | 2/2006 | Nakayama et al. |
| 2006/0074191 A1 | 4/2006 | DesNoyer et al. |
| 2006/0093842 A1 | 5/2006 | DesNoyer et al. |
| 2006/0115455 A1 | 6/2006 | Reed et al. |
| 2006/0121012 A1 | 6/2006 | Kutryk et al. |
| 2006/0135476 A1 | 6/2006 | Kutryk et al. |
| 2006/0159918 A1 | 7/2006 | Dugan et al. |
| 2006/0177416 A1 | 8/2006 | Turnell et al. |
| 2006/0188469 A1 | 8/2006 | Turnell et al. |
| 2006/0188486 A1 | 8/2006 | Carpenter et al. |
| 2006/0222546 A1 | 10/2006 | Lee et al. |
| 2006/0224331 A1 | 10/2006 | Watson Michnick et al. |
| 2006/0286064 A1 | 12/2006 | Turnell et al. |
| 2007/0042017 A1 | 2/2007 | Kutryk et al. |
| 2007/0055367 A1 | 3/2007 | Kutryk et al. |
| 2007/0066541 A1 | 3/2007 | Hughes et al. |
| 2007/0071790 A1 | 3/2007 | Ameer et al. |
| 2007/0077272 A1 | 4/2007 | Li et al. |
| 2007/0106035 A1 | 5/2007 | Gomurashvili et al. |
| 2007/0128250 A1 | 6/2007 | Katsarava et al. |
| 2007/0134332 A1 | 6/2007 | Turnell et al. |
| 2007/0141100 A1 | 6/2007 | Sung et al. |
| 2007/0141107 A1 | 6/2007 | Kutryk et al. |
| 2007/0156232 A1 | 7/2007 | Kutryk et al. |
| 2007/0160622 A1 | 7/2007 | Turnell et al. |
| 2007/0167605 A1 | 7/2007 | Chu et al. |
| 2007/0191932 A1 | 8/2007 | Kutryk et al. |
| 2007/0196422 A1 | 8/2007 | Kutryk et al. |
| 2007/0213801 A1 | 9/2007 | Kutryk et al. |
| 2007/0282011 A1 | 12/2007 | Gomurashvili et al. |
| 2007/0287987 A1 | 12/2007 | Katsarava et al. |
| 2007/0292476 A1 | 12/2007 | Landis et al. |
| 2007/0298476 A1 | 12/2007 | Landis et al. |
| 2007/0299155 A1 | 12/2007 | Carpenter et al. |
| 2008/0020015 A1 | 1/2008 | Carpenter et al. |
| 2008/0050419 A1 | 2/2008 | Katsarava et al. |
| 2008/0057024 A1 | 3/2008 | Zhang et al. |
| 2008/0160089 A1 | 7/2008 | Vitiello et al. |
| 2008/0288057 A1 | 11/2008 | Carpenter et al. |
| 2008/0299174 A1 | 12/2008 | Gomurashvili et al. |
| 2009/0022772 A1 | 1/2009 | Carpenter et al. |
| 2009/0029937 A1 | 1/2009 | Chu et al. |
| 2009/0068743 A1 | 3/2009 | Turnell et al. |
| 2009/0202620 A1 | 8/2009 | Turnell et al. |
| 2009/0232874 A1 | 9/2009 | Chu et al. |
| 2009/0238854 A1 | 9/2009 | Pacetti et al. |
| 2009/0253809 A1 | 10/2009 | Gomurashvili et al. |
| 2010/0004066 A1 | 1/2010 | Kowalski |
| 2010/0004390 A1 | 1/2010 | Turnell et al. |
| 2010/0040664 A1 | 2/2010 | Katsarava et al. |
| 2011/0027379 A1 | 2/2011 | Chu et al. |
| 2011/0137406 A1 | 6/2011 | Carpenter et al. |
| 2012/0027859 A1 | 2/2012 | Turnell et al. |
| 2012/0282299 A1 | 11/2012 | Delamarre et al. |
| 2012/0328706 A1 | 12/2012 | Turnell et al. |
| 2014/0105957 A1 | 4/2014 | Franken et al. |
| 2014/0120170 A1 | 5/2014 | Mihov et al. |
| 2014/0179802 A1 | 6/2014 | Franken et al. |
| 2014/0220099 A1 | 8/2014 | Draaisma et al. |
| 2015/0038415 A1 | 2/2015 | Zupancich |
| 2015/0216987 A1 | 8/2015 | Thies et al. |
| 2015/0240387 A1 | 8/2015 | Gillissen-Van Der Vight |
| 2015/0246001 A1 | 9/2015 | Zupancich et al. |
| 2015/0328374 A1 | 11/2015 | Mihov et al. |

FOREIGN PATENT DOCUMENTS

| | | |
|---|---|---|
| CA | 2225792 | 11/1997 |
| CA | 2419429 | 3/2002 |
| CA | 2419429 | 7/2010 |
| CN | 1281355 | 1/2001 |
| CN | 1296852 | 5/2001 |
| CN | 1837259 | 9/2006 |
| CN | 101168595 | 10/2006 |
| CN | 10168595 | 4/2008 |
| DE | 4224401 | 1/1994 |
| EP | 0147780 | 7/1985 |
| EP | 0147780 A3 | 3/1987 |
| EP | 0396429 | 11/1990 |
| EP | 0447719 | 9/1991 |
| EP | 0447719 B1 | 11/1993 |
| EP | 0396429 B1 | 7/1996 |
| EP | 00926184 | 12/1998 |
| EP | 0926184 | 6/1999 |

(56) References Cited

FOREIGN PATENT DOCUMENTS

| | | |
|---|---|---|
| EP | 0932399 | 1/2006 |
| EP | 0932399 B1 | 1/2006 |
| EP | 1313794 | 11/2006 |
| EP | 1313794 B1 | 11/2006 |
| EP | 1945682 | 7/2008 |
| EP | 19945682 | 7/2008 |
| JP | 2008027269 | 1/1996 |
| JP | 2005139139 | 6/2005 |
| JP | 2008027269 | 7/2008 |
| JP | 2008542393 | 11/2008 |
| WO | WO1994004642 | 3/1994 |
| WO | WO1997030104 | 8/1997 |
| WO | WO1998031398 | 7/1998 |
| WO | WO1998032398 | 7/1998 |
| WO | WO9929303 | 6/1999 |
| WO | WO99029302 | 6/1999 |
| WO | WO1999029302 | 6/1999 |
| WO | WO199058151 | 11/1999 |
| WO | WO1999058151 | 11/1999 |
| WO | WO1999061916 | 12/1999 |
| WO | WO2001028591 | 4/2001 |
| WO | WO2001051027 | 7/2001 |
| WO | WO2011146483 | 11/2001 |
| WO | WO2001091703 | 12/2001 |
| WO | WO2002018477 | 3/2002 |
| WO | WO2002018477 A2 | 3/2002 |
| WO | WO20020018477 | 3/2002 |
| WO | WO03024420 | 3/2003 |
| WO | WO2003024420 | 3/2003 |
| WO | WO2003062298 | 7/2003 |
| WO | WO2004039944 | 5/2004 |
| WO | WO2004040339 | 5/2004 |
| WO | WO2005027906 | 3/2005 |
| WO | WO2005061024 | 7/2005 |
| WO | WO2005097186 | 10/2005 |
| WO | WO2005112587 | 12/2005 |
| WO | WO2005112884 | 12/2005 |
| WO | WO2005118681 | 12/2005 |
| WO | WO2006050091 | 5/2006 |
| WO | WO2006083874 | 8/2006 |
| WO | WO2006088647 | 8/2006 |
| WO | WO2006108167 | 10/2006 |
| WO | WO2006132950 | 12/2006 |
| WO | WO2007035938 | 3/2007 |
| WO | WO2007035938 A2 | 3/2007 |
| WO | WO1997030104 | 4/2007 |
| WO | WO2007038246 | 4/2007 |
| WO | WO2007050415 | 5/2007 |
| WO | WO2007067744 | 6/2007 |
| WO | WO2007089870 | 8/2007 |
| WO | WO2007089931 | 8/2007 |
| WO | WO20070089931 | 8/2007 |
| WO | WO2007130477 | 11/2007 |
| WO | WO2007133616 | 11/2007 |
| WO | WO2008048298 | 4/2008 |
| WO | WO20080048298 | 4/2008 |
| WO | WO2008157254 | 12/2008 |
| WO | WO2009012449 | 1/2009 |
| WO | WO2009012449 A1 | 1/2009 |
| WO | WO2009015143 | 1/2009 |
| WO | WO2009026543 | 2/2009 |
| WO | WO20100045241 | 4/2010 |
| WO | WO2011045443 | 4/2011 |
| WO | WO2011045443 A1 | 4/2011 |
| WO | WO2011146483 | 11/2011 |
| WO | WO2012175746 | 12/2012 |
| WO | WO2012175748 | 12/2012 |
| WO | WO2007038246 | 4/2017 |

OTHER PUBLICATIONS

Eccleston, et al., pH-responsive pseudo-peptides for cell membrane disruption, Journal of Controlled Release 2000, p. 297-307, vol. 69, No. 2.

Eccleston, et al., Synthetic routes to responsive polymers, Reactive & Functional Polymers, 1999, p. 147-161, vol. 42, No. 2.

Gautier, et al., Alkylated poly (L-lysine citramide) as models to investigate the ability, Journal of Controlled Release 1999, p. 235-247, vol. 60, No. 2-3.

Final Office Action dated Apr. 12, 2017 in U.S. Appl. No. 14/432,349.

Asin, et al., Sequential Poly(ester amide)s based on Glycine, Diols, and Dicarboxylic Acids: Thermal Polyesterification verus Interfacial Polyamidation. Characterization of Polymers Containing Stiff Units, J. Polym. Sci. Part A: Polm Chem, 2001, 4283-4293, 39(24).

Becker, et al., Prevention of Postoperative Abdominal Adhesions by a Sodium Hyaluronate-Based Bioresorbable Membrane: A Prospective, Randomized, Double-Multicenter Study, J. Am. Coll. Surg, 1996, pp. 297-306, 183.

Eccleston et al, pH-responsive pseudo-peptides for cell membrane disruption, Journal of Controlled Release, 2000, pp. 297-307, vol. 69, No. 2.

Eccleston et al., Synthetic routes to responsive polymers, Reactive & Functional Polymers, 1999, pp. 147-161, vol. 42, No. 2.

Furchgott and Zawadzki, The obligatory role of endothelial cells in the relaxation of arterial smooth muscle by acetylcholine, Inature, 1980, pp. 373-376, 388.

Gautier et al, Alkylated poly(L-lysine citramide) as models to investigate the ability, Journal of Controlled release, 1999, pp. 235-247, vol. 60, No. 2-3.

Gomurashvili , et al, Amino Acid Based Bioanalogous Polymers. Synthesis and Study of New Poly(Ester Amide)S Composed of Hydrophobic α-Amino Acids and Dianhydrohexitoles, J.M.S.—Pure Appl. Chem, 2000, pp. 215-227, A37(3).

Gomurashvili, et al., From Drug-Eluting Stents to Biopharmaceuticals: Poly(ester amide) a Versatile New Bioabsorable Biopolymer. In: Polymers for Biomedical Applications, ACS Symposium Series; American Chemical Society, 2008, pp. 10-26, Chapter 2.

Guo, et al., Synthesis and Characterization of Novel Biodegradable Unsaturated Poly(ester amide)/Poly(ethylene glycol) Diacrylate Hydrogels, Journal of Polymer Science: Part A: Polymer Chemistry, 2005, pp. 3932-3944, 43.

Huang, et al., Biodegradable Polymers: Chymotrypsin Degradationi of a Low Molecular Weight Poly(ester-Urea) Containing Phenylalanine, J. Appl. Polym. Sci, 1979, pp. 429-437, 23.

Kartvelishvili, et al., Ämino acid based bioanalogous polymers. Novel regular poly(ester urethane)s and poly(ester urea)s based on bis(L-phenylalanine) α, Ω-alkylene diesters, Macromol. Chem. Phys, 1997, pp. 1921-1932, 198.

Qian, et al., Preparation of biodegradable polyesteramide microspheres, Colloid Polym. Sci, 2004, pp. 1083-1088, 282.

Saotome et al, Novel Enzymatically Degradable Polymers Comprising a-Amino Acid, 1,2-Ethanediol, and Adipic Acid, Chemistry Letters, 1991, pp. 21-24, No Volume.

Tsitlanadze et al., Biodegradation of amino-acid-based poly(ester amide)s: in vitro weight loss and preliminary in vivo studies, Journal of Biomaterials Science, Jan. 1, 2004, 24 Pages, vol. 15.

Yokoe et al, Biodegradable Polymers Based on Renewable Resources. VII. Novel Random and Alternating Copolycarbonates from 1,4:3,6-Dianhydrohexitols and Aliphatic Diols, Journal of Polymer Science: Part A: Polymer Chemistry, 2003, pp. 2312-2331, 41.

Final Office Action in U.S. Appl. No. 14/432,349 dated Apr. 12, 2017.

Asin et al., "Sequential Poly(ester amide)s Based on Glycine, Diols, and Dicarboxylic Acids: Thermal Polyesterification versus Interfacial Polyamidation. Characterization of Polymers Containing Stiff Units," J. Polym.Sci, Part A: Polym. Chem., 39(24):4283-4293 (2001).

Becker et al., "Prevention of Postoperative Abdominal Adhesions by a Sodium Hyaluronate-Based Bioresorbable Membrane: A Prospective, Randomized, Double-Blind Multicenter Study", J. Am. Coll. Surg., 183:297-306 (1996).

Furchgott and Zawadzki, "The obligatory role of endothelial cells in the relaxation of arterial smooth muscle by acetylcholine", Inature, 288:373-376 (1980).

(56) References Cited

OTHER PUBLICATIONS

Gomurashvili et al., "Amino Acid Based Bioanalogous Polymers. Synthesis and Study of New Poly(Ester Amide)S Composed of Hydrophobic α-Amino Acids and Dianhydrohexitoles", J.M.S.—Pure Appl. Chem., A37(3):215-227 (2000).

Gomurashvili et al., "From Drug-Eluting Stents to Biopharmaceuticals: Poly(ester amide) a Versatile New Bioabsorable Biopolymer. In: Polymers for Biomedical Applications", ACS Symposium Series; American Chemical Society, Chapter 2, pp. 10-26 (2008).

Guo et al., "Synthesis and Characterization of Novel Biodegradable Unsaturated Poly(ester amide)/Poly(ethylene glycol) Diacrylate Hydrogels", Journal of Polymer Science: Part A: Polymer Chemistry, 43:3932-3944 (2005).

Huang et al., "Biodegradable Polymers: Chymotrypsin Degradationi of a Low Molecular Weight Poly(ester-Urea) Containing Phenylalanine", J. Appl. Polym. Sci., 23:429-437 (1979).

Kartvelishvili et al., Amino acid based bioanalogous polymers. Novel regular poly(ester urethane)s and poly(ester urea)s based on bis(L-phenylalanine) α, Ω-alkylene diesters, Macromol. Chem. Phys., 198:1921-1932 (1997).

Qian et al., "Preparation of biodegradable polyesteramide microspheres", Colloid Polym. Sci., 282:1083-1088 (2004).

Saotome et al., "Novel Enzymatically Degradable Polymers Comprising a-Amino Acid, 1,2-Ethanediol, and Adipic Acid", Chemistry Letters, pp. 21-24 (1991).

Tsitlanadze et al., "Biodegradation of amino-acid-based poly(ester amide)s: in vitro weight loss and preliminary in vivo studies", Journal of Biomaterials Science. Polymer Edition, VSP, Utretch, NL, vol. 15, Jan. 1, 2014, pp. 1-24.

Yokoe et al., "Biodegradable Polymers Based on Renewable Resources. VII. Novel Random and Alternating Copolycarbonates from 1,4:3,6-Dianhydrohexitols and Aliphatic Diols", Journal of Polymer Science: Part A: Polymer Chemistry, 41:2312-2331 (2003).

Nov. 9, 2016 Non-Final Office Action in U.S. Appl. No. 14/432,349.

Aug. 19, 2016 Non-Final Office Action in U.S. Appl. No. 14/128,839.

U.S. Appl. No. 14/432,349 Non Final Office Action dated Aug. 23, 2017.

* cited by examiner

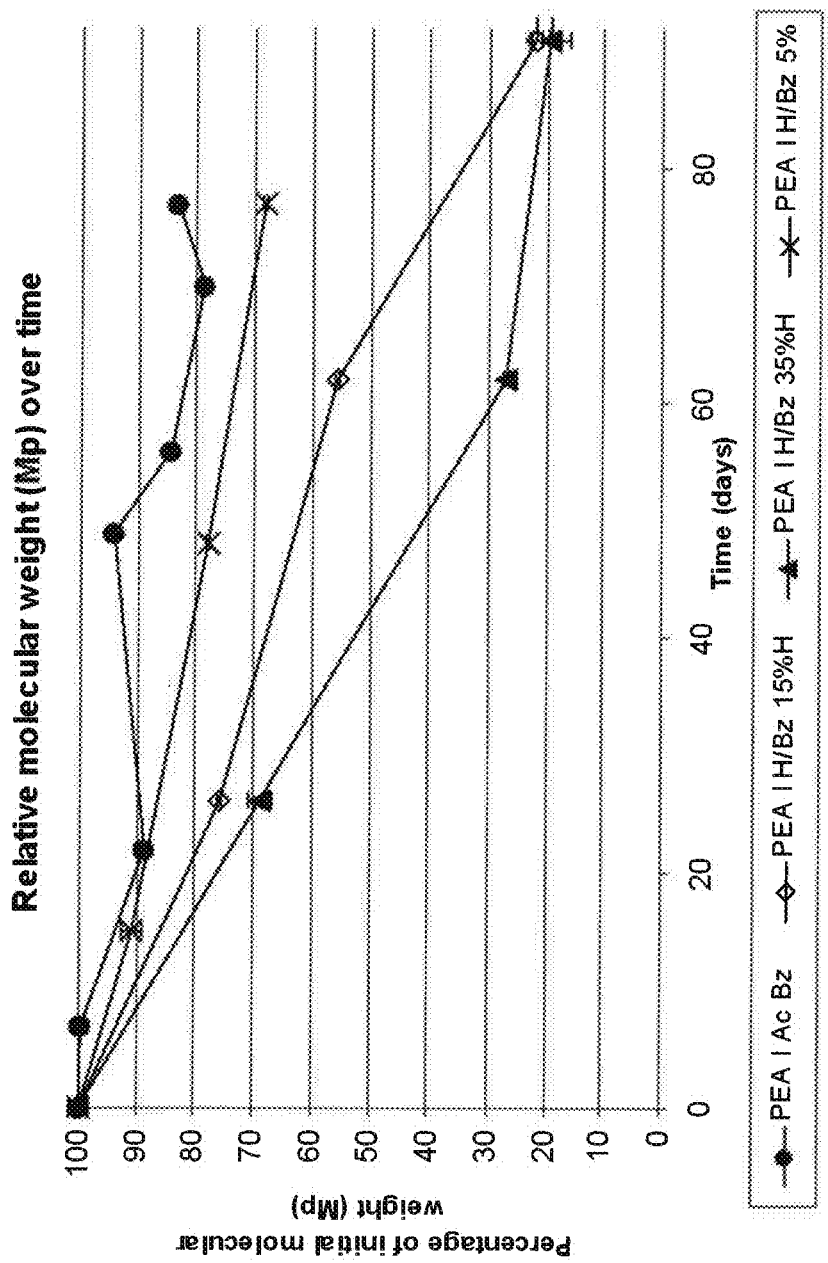

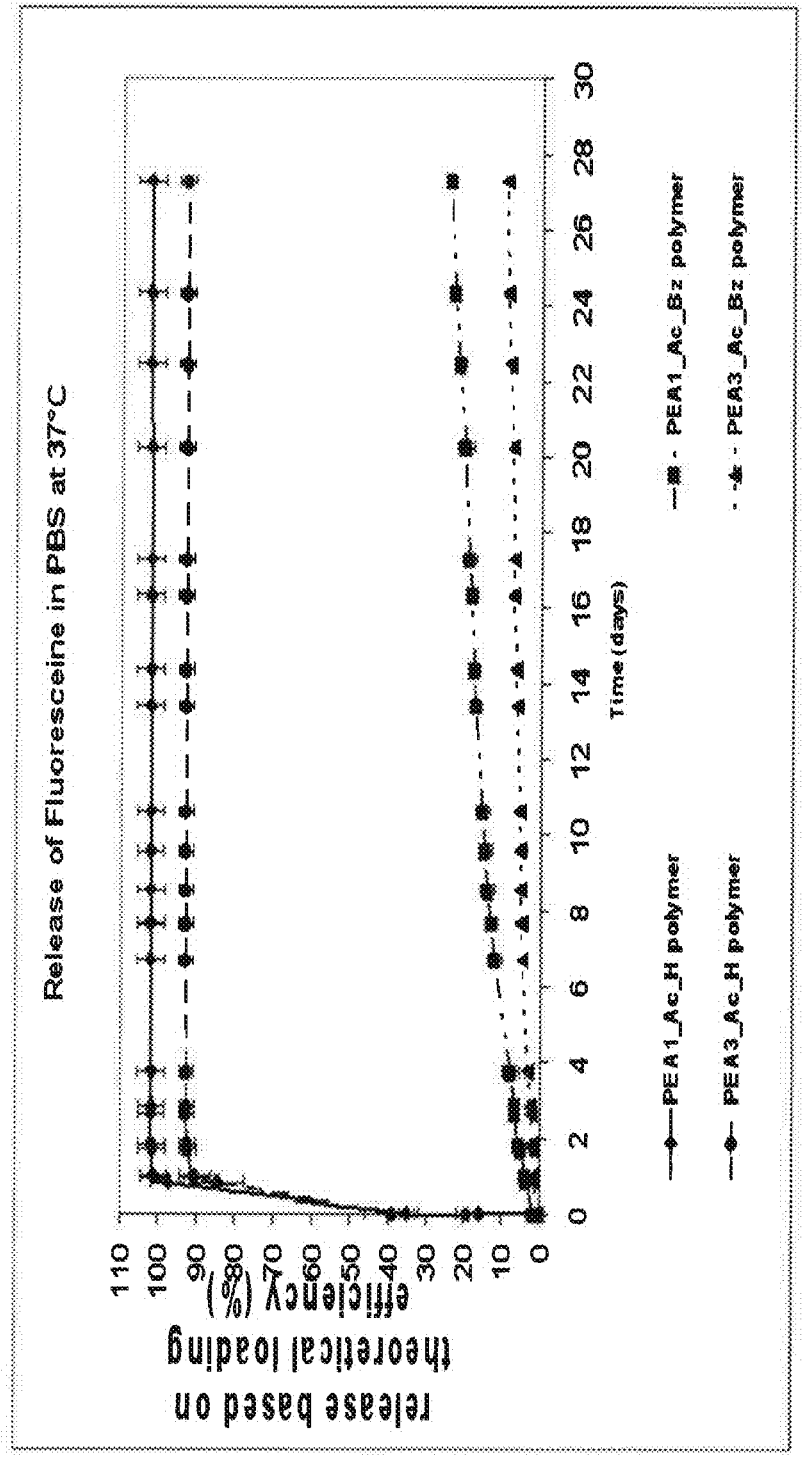

BIODEGRADABLE POLYESTERAMIDE COPOLYMERS FOR DRUG DELIVERY

CROSS-REFERENCE TO RELATED APPLICATIONS

This application is a divisional application of U.S. application Ser. No. 14/128,839, filed Mar. 28, 2014, which is a 371 of International Application PCT/EP2012/062265, filed Jun. 25, 2012, which claims priority to European Appl. No. EP 11171191.7 filed Jun. 23, 2011, each of which is hereby incorporated by reference in its entirety.

FIELD

The present invention relates to new biodegradable polyesteramide copolymers. The present invention also relates to the polyesteramide copolymers for use in medical applications especially for use in drug delivery.

BACKGROUND

Biodegradable polyesteramides are known in the art, in particular α-amino acid-diol-diester based polyesteramides (PEA) are known from G. Tsitlanadze, et al. J. Biomater. Sci. Polym. Edn. (2004) 15:1-24. These polyesteramides provide a variety of physical and mechanical properties as well as biodegradable profiles which can be adjusted by varying three components in the building blocks during their synthesis: naturally occurring amino acids and, therefore, hydrophobic alpha-amino acids, non-toxic fatty diols and aliphatic dicarboxylic acids.

WO2002/18477 specifically refers to alpha-amino acid-diol-diester based polyesteramides (PEA) copolymers of formula I, further referred to as PEA-I, wherein:
m varies from 0.1 to 0.9; p varies from 0.9 to 0.1; n varies from 50 to150;
each R1 is independently $(C1-C_{20})$alkylene;
each $R_2$ is independently hydrogen or $(C_6-C_{10})$aryl$(C1-C_6)$alkyl;
each $R_3$ is independently hydrogen, $(C1-C_6)$ alkyl, $(C_2-C_6)$alkenyl, $(C_2-C_6)$alkynyl, or $(C_6-C_{10})$aryl$(C_1-C_6)$ alkyl; and
each $R_4$ is independently $(C_2-C_{20})$alkylene.

PEA-I is a random copolymer comprising m units build upon alpha-amino acids, diols and an aliphatic dicarboxylic acids, which are copolymerized with p units build upon an aliphatic dicarboxylic acid and L-lysine. The $R_2$ in the amino acid L-lysine is either H (hereinafter referred to PEA-I-H) or a $(C_6-C_{10})$aryl$(C1-C_6)$alkyl from which benzyl is the most preferred. In case that the $R_2$ in L-lysine of PEA-I comprises benzyl it is further referred to as (PEA-I-Bz).

It has been recognized that PEA-I-H shows high swelling profiles which results in a fast degradation and a quick burst release of bioactive agents in approximately 24-48 hours. These properties have reduced the attention of PEA-I-H polymers as materials with potential in drug delivery. It has also been recognized that PEA-I-H enzymatically degrades very fast, for example in vitro it completely degrades in 1 week. On the other hand it has been recognized that PEA-I-Bz provides a more sustained release of bioactive agents over a prolonged period of time. Moreover it shows minor if any swelling properties. PEA-I-Bz enzymatically degrades slowly and the in-vivo degradation of the polymer strongly depends of the administration site, tissue response and health status of the studied model. However, PEA-I-Bz lacks the ability to degrade hydrolytically in absence of enzymes which could result in too slow or even non complete degradation of the polymer.

The same disadvantages appear to be true for another type of prior art PEA random co-polymers according to Formula II which comprise at least two linear saturated or unsaturated aliphatic diol residues into two bis-(a amino acid)-based diol diesters. These copolymers are for example disclosed in WO2008/0299174.

Formula I

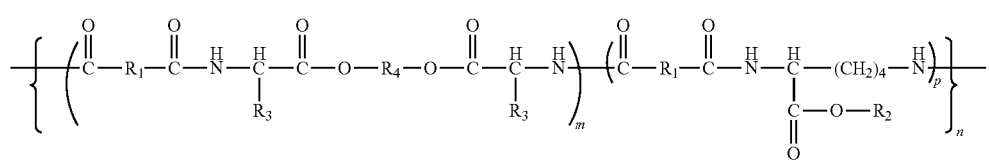

Formula II

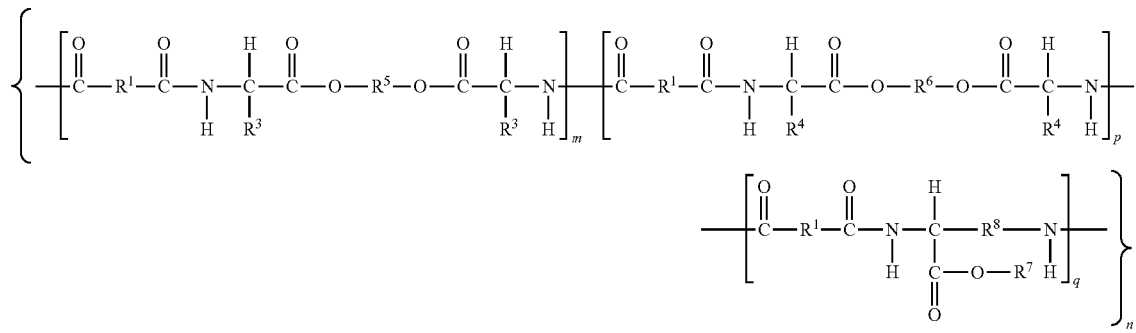

In a preferred embodiment of above polyesteramide co-polymer m varies from 0.01 to 0.99; p varies from 0.2 to 3 and q varies from 0.10 to 1.00 whereby n is 5 to 100; $R_1$ is —$(CH_2)_8$; $R_3$ and $R_4$ in the backbone units m and p is leucine, —$R_5$ is hexane, and $R_6$ is a bicyclic-fragments of 1,4:3,6-dianhydrohexitols of structural formula (III);

Formula III

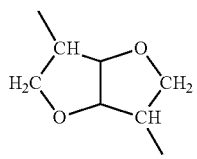

$R_7$ may be chosen from H or a benzyl group and $R_8$ is —$(CH2)4$-.

The object of the present invention is therefore to provide new biodegradable polyesteramide random copolymers which take away the above disadvantages.

A further object of the present invention is to provide new biodegradable polyesteramide copolymers which show a sustained release in a controllable way.

Another object of the present invention is to provide new biodegradable polyesteramide copolymers which on top of surface erosion degradation which is caused enzymatically, also shows degradation via a hydrolytic bulk erosion mechanism.

The object of the present invention is achieved by providing a biodegradable poly(esteramide) random copolymer (PEA) according to structural formula (IV), Formula IV

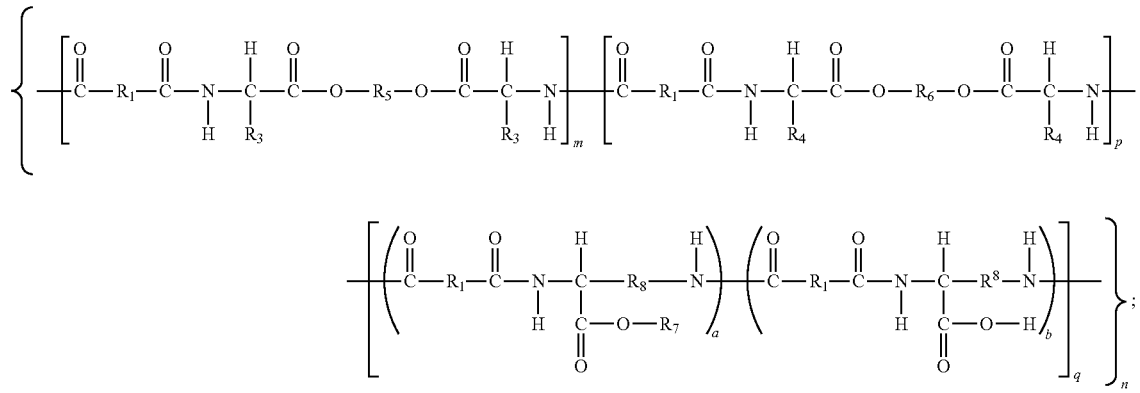

If $R_7$ is H the polymer is further indicated as PEA-III-H, if $R_7$ is benzyl, the polymer is further indicated as PEA-III-Bz.

SUMMARY

Because of the above described disadvantages of PEA-I-H, PEA-I-Bz PEA-III-H and PEA-III-Bz it seems that these prior art polyesteramides do not fully provide the properties of releasing bioactive agents in a consistent and reliable manner. Moreover they do not provide a satisfying degradation profile. It is either too fast or too slow degrading or only enzymatically and not hydrolytically degrading.

wherein
  m+p varies from 0.9-0.1 and q varies from 0.1 to 0.9
  m+p+q=1 whereby m or p can be 0
  n varies from 5 to 300;
  $R_1$ is independently selected from the group consisting of ($C_2$-$C_{20}$) alkylene, ($C_2$-$C_{20}$) alkenylene, —($R_9$—CO—O—$R_{10}$—O—CO—$R_9$)—, —$CHR_{11}$—O—CO—$R_{12}$—$COOCR_{11}$— and combinations thereof;
  $R_3$ and $R_4$ in a single backbone unit m or p, respectively, are independently selected from the group consisting of hydrogen, ($C_1$-$C_6$)alkyl, ($C_2$-$C_6$)alkenyl, ($C_2$-$C_6$)alkynyl, $(C_6-C_{10})$aryl, $(C_1-C_6)$alkyl, —$(CH_2)SH$, —$(CH_2)_2S(CH_3)$, —$CH_2OH$, —$CH(OH)CH_3$, —$(CH_2)_4NH_3+$, —$(CH_2)_3NHC(=NH_2+)NH_2$, —$CH_2COOH$, —$(CH_2)COOH$, —$CH_2$—$CO$—$NH_2$, —$CH_2CH_2$—$CO$—$NH_2$, —$CH_2CH_2COOH$, $CH_3$—$CH_2$—$CH(CH_3)$—, $(CH_3)_2$—$CH$—$CH_2$—, $H_2N$—$(CH_2)_4$—, $Ph$-$CH_2$—, $CH=C$—$CH_2$—, $HO$-$p$-$Ph$-$CH_2$—, $(CH_3)_2$—$CH$—, $Ph$-$NH$—, $NH$—$(CH_2)_3$—$C$—, $NH$—$CH=N$—$CH=C$—$CH_2$—.

$R_5$ is selected from the group consisting of $(C_2-C_{20})$ alkylene, $(C_2-C_{20})$alkenylene, alkyloxy or oligoethyleneglycol $R_6$ is selected from bicyclic-fragments of 1,4:3,6-dianhydrohexitols of structural formula (III);

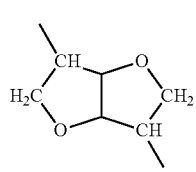

Formula III $R_7$ is selected from the group consisting of $(C_6-C_{10})$aryl $(C_1-C_6)$alkyl $R_8$ is —$(CH_2)_4$—;

$R_9$ or $R_{10}$ are independently selected from $C_2-C_{12}$ alkylene or $C_2-C_{12}$ alkenylene.

$R_{11}$ or $R_{12}$ are independently selected from H, methyl, $C_2-C_{12}$ alkylene or $C_2-C_{12}$ alkenylene and whereby a is at least 0.05, b is at least 0.05 and a+b=1.

BRIEF DESCRIPTION OF THE DRAWINGS

FIG. 8: Hydrolytic degradation of PEA-I-Bz compared to PEA-I-H/Bz (comprising 15% H, 35% H and 5% H).

FIG. 9: Release of Fluoresceine in PBS from PEA-I-H, PEA-I-Bz and PEA-III-H/PEA-III-Bz.

DETAILED DESCRIPTION

Surprisingly it has been found that polyesteramides of formula IV in which both L-Lysine-H as well as L-lysine-benzyl are present, (hereinafter referred to as PEA-H/Bz) provide unexpected properties in terms of swelling, release and degradation properties. It has been found that PEA-H/Bz co-polymers provide a sustained release of bioactive agents and provide a hydrolytic degradation profile in contrast to the prior art polyesteramides.

Figure 4:
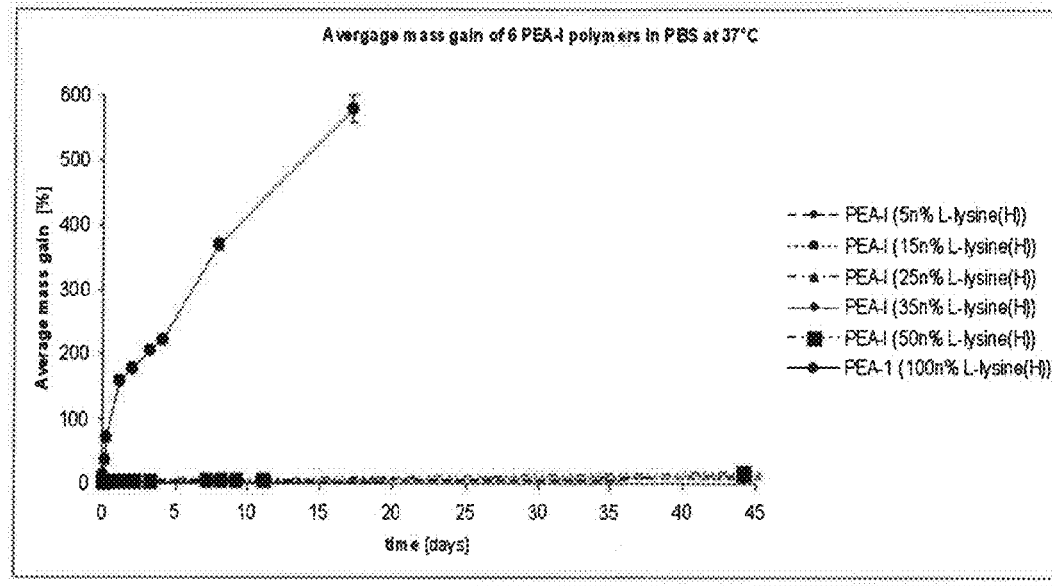
FIG. 4: Average mass gain in % in time of PEA-I-H/Bz polymers comprising (5-, 25-, 50-, 100% (H)).

It is unexpected that the swelling of PEA-I-H is very high and the swelling of PEA-I-Bz is very low whereas the swelling of the PEA-I-H/Bz copolymers according to the present invention shows a profile comparable to the swelling profile of PEA-I-Bz. This is shown in FIG. 4.

Figure 6:
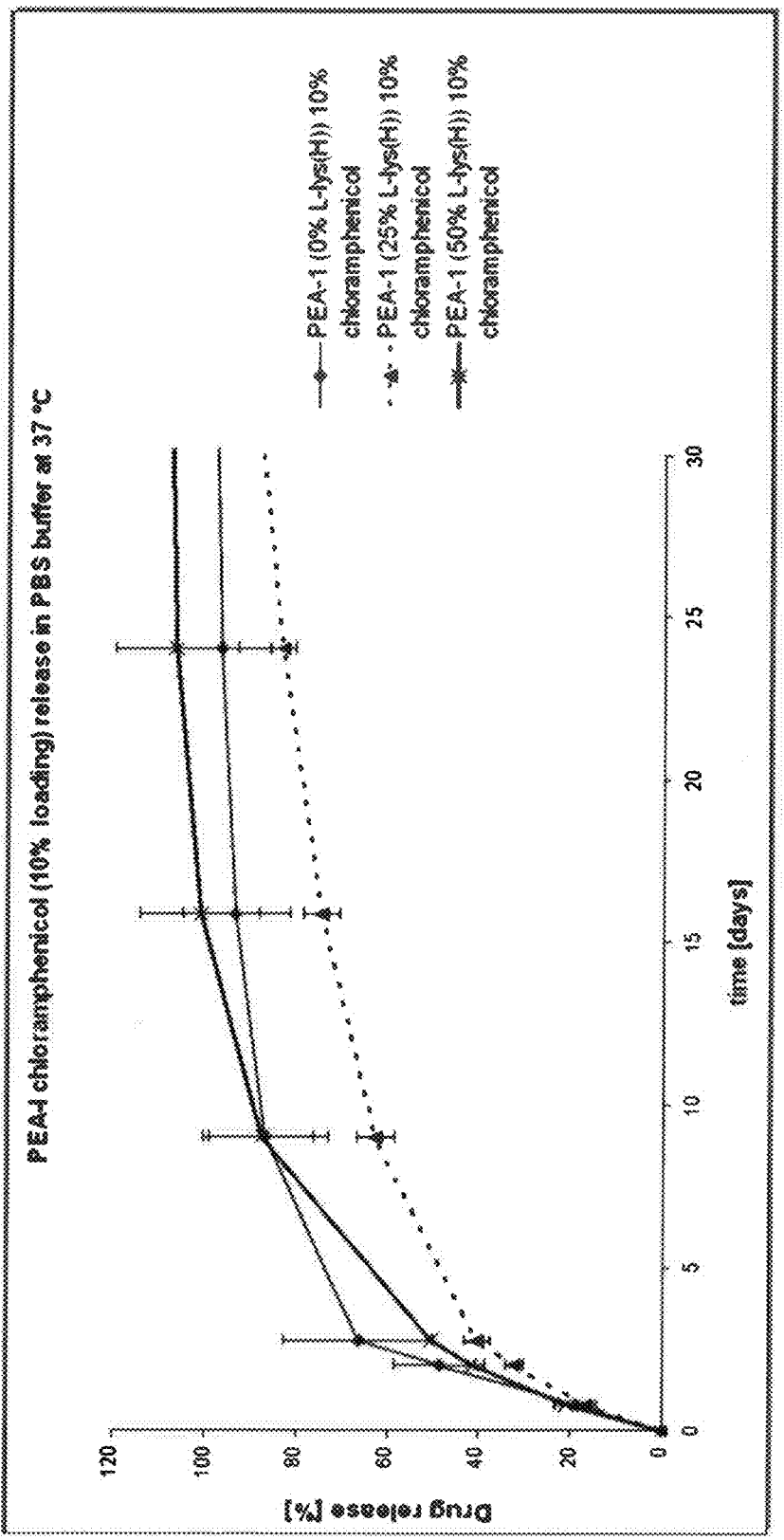
FIG. 6: In vitro release of chloramphenicol (10% loading) from PEA I-H/Bz polymers comprising (0% H, 25% H and 50% H)).

Swelling properties are directly related to release properties. FIG. 6 shows the release of Chloramphenicol (10% loading) from PEA-I-Bz (0% L-lysine-H) compared to PEA-I-H/Bz co-polymers comprising 25% L-Lysine-H and 50% L-lysine-H The figure clearly shows that PEA-III-H/Bz 50% H films do release chloramphenicol over period of a month, just slightly faster than PEA-III-Bz. This observation emphasized that the drug elution properties of PEA-III-H/Bz 50% H are comparable to the art would expect that both swelling and drug elution properties of PEA-III-H/Bz-(50% H) are somewhere in between of these of the two extremes PEA-III-Bz (0% H) and PEA-III-H(100% H). Even more surprising PEA-III-H/Bz 25% H does provide a more sustained release of chloramphenicol than PEA-III-Bz.

Furthermore, it has surprisingly been found that the properties of the newly synthesized PEA-H/Bz co-polymers cannot be achieved via mechanical blending of the corresponding PEA-H and PEA-Bz polymers. This is further evidenced in FIG. 7 which shows that PEA-I-H/Bz 25% H shows a different swelling behavior than the mechanical blend containing 25 wt % PEA-I-H and 75 wt % PEA-I-Bz. The same findings are valid for PEA-I-H/Bz comprising 35% H. This implies that drug elution properties and degradation of the PEA-H/Bz polymers also cannot be matched by mechanical blending of PEA-Bz and PEA-H polymers.

Despite the newly synthesized PEA-H/Bz co-polymers show a little swelling, their degradation properties are markedly different than for the prior art polymers PEA-I-Bz and PEA-III-Bz. It has been found that PEA-I-H/Bz co-polymers seem to degrade hydrolytically and via bulk erosion mechanism whereas it is known that prior art PEA's (PEA-I-Bz, PEA-III-Bz) degrade only via an enzymatic degradation process and via a surface erosion mechanism.

In summary the PEA H/Bz polymers provide a good solution for sustained drug delivery and degrade hydrolytically in contrast to the prior art PEA Bz polymers. Also other prior art polymers such as PLGA or PLLA seem to degrade mainly via bulk erosion mechanism. This is confirmed in FIG. 8.

It is moreover known that the degradation of PLGA and PLLA will result in a pH drop which is undesired because it may influence the stability of the bioactive agent to be released from the polymers. From experiments it has surprisingly been found that the newly designed polymers PEA H/Bz do not show a significant pH drop.

The above findings confirm that the polyesteramides of formula IV in which both L-Lysine-H as well L-lysine-benzyl are present in a certain ratio is a new class of polymers with surprising properties addressing better the needs of polymers for drug delivery.

In the following embodiments of the present invention n preferably varies from 50-200 whereby a may be at least 0.15, more preferably at least 0.5, most preferably at least 0.8, even more preferably at least 0.85.

In one embodiment in biodegradable polyesteramide copolymer according to Formula (IV) comprises p=0 and m+q=1 whereby m=0.75, a=0.5 and a+b=1, $R_1$ is $(CH_2)_8$, $R_3$ is —$(CH_3)_2$—CH—$CH_2$—, $R_5$ is hexyl, $R_7$ is benzyl and $R_8$ is —$(CH_2)_4$— This polyesteramide is referred to as PEA-I-H/Bz 50% H.

In another preferred embodiment of the present invention the biodegradable polyesteramide copolymer according to Formula (IV) comprises m+p+q=1, q=0.25, p=0.45 and m=0.3 whereby a is 0.5 and a+b=1 and whereby $R_1$ is —$(CH_2)_8$; $R_3$ and $R_4$ respectively are —$(CH_3)_2$—CH—$CH_2$—, $R_5$ is selected from the group consisting of $(C_2$-$C_{20})$ alkylene, $R_6$ is selected from bicyclic-fragments of 1,4:3,6-dianhydrohexitols of structural formula (III), $R_7$ is benzyl and $R_8$ is —$(CH_2)_4$—. This polyesteramide is referred to as PEA-III-H/Bz 50% H.

In a still further preferred embodiment of the present invention the biodegradable polyesteramide copolymer according to Formula (IV) comprises m+p+q=1, q=0.25, p=0.45 and m=0.3 whereby a is 0.75 and a+b=1, $R_1$ is —$(CH_2)_8$; $R_4$ is $(CH_3)_2$—CH—$CH_2$—, $R_7$ is benzyl, $R_8$ is —$(CH_2)_4$— and $R_6$ is selected from bicyclic fragments of 1,4:3,6-dianhydrohexitols of structural formula (III). This polyesteramide is referred to as PEA-III-H/Bz 25% H.

In a yet further preferred embodiment of the present invention the biodegradable polyesteramide copolymer according to Formula (IV) comprises m+p+q=1, q=0.1, p=0.30 and m=0.6 whereby a=0.5 and a+b=1, $R_1$ is —$(CH_2)_4$; $R_3$ and $R_4$ respectively, are $(CH_3)_2$—CH—$CH_2$—; $R_5$ is selected from the group consisting of $(C_2$-$C_{20})$ alkylene, $R_7$ is benzyl, $R_8$ is —$(CH_2)_4$— and $R_6$ is selected from bicyclic-fragments of 1,4:3,6-dianhydrohexitols of structural formula (III). This polyesteramide is referred to as PEA-II-H/Bz50% H.

As used herein, the term "alkyl" refers to a straight or branched chain hydrocarbon group including methyl, ethyl, n-propyl, isopropyl, n-butyl, isobutyl, tert-butyl, n-hexyl, and the like.

As used herein, the term "alkylene" refers to a divalent branched or unbranched hydrocarbon chain containing at least one unsaturated bond in the main chain or in a side chain.

As used herein, the term "alkenyl" refers to a straight or branched chain hydrocarbon group containing at least one unsaturated bond in the main chain or in a side chain.

As used herein, "alkenylene", refers to structural formulas herein to mean a divalent branched or unbranched hydrocarbon chain containing at least one As used herein, "alkynyl", refers to straight or branched chain hydrocarbon groups having at least one carbon-carbon triple bond.

The term "aryl" is used with reference to structural formulas herein to denote a phenyl radical or an ortho-fused bicyclic carbocyclic radical having about nine to ten ring atoms in which at least one ring is aromatic. Examples of aryl include, but are not limited to, phenyl, naphthyl, and nitrophenyl.

The term biodegradable" refers to material which is capable of being completely or substantially degraded or eroded when exposed to an in vivo environment or a representative in vitro. A polymer is capable of being degraded or eroded when it can be gradually broken-down, resorbed, absorbed and/or eliminated by, for example, hydrolysis, enzymolysis, oxidation, metabolic processes, bulk or surface erosion, and the like within a subject. The terms "bioabsorbable" and "biodegradable" are used interchangeably in this application.

The term "random" as used herein refers to the distribution of the m, p and q units of the polyesteramide of formula (IV) in a random distribution.

At least one of the alpha-amino acids used in the polyesteramide co-polymers is a natural alpha-amino acid. For example, when the $R_3$s or $R_4$s are $CH_2Ph$, the natural alpha-amino acid used in synthesis is L-phenylalanine. In alternatives wherein the $R_3$s or $R_4$s are —$CH_2$—$CH(CH_3)_2$, the co-polymer contains the natural amino acid, leucine. By independently varying the $R_3$s and $R_4$s within variations of the two co-monomers as described herein, other natural alpha-amino acids can also be used, e.g., glycine (when the $R_3$s or $R_4$s are H), alanine (when the $R_3$s or $R_4$s are $CH_3$), valine (when the $R_3$s or $R_4$s are $CH(CH_3)_2$), isoleucine (when the $R_3$s or $R_4$s are $CH(CH_3)$—$CH_2$—$CH_3$), phenylalanine (when the $R_3$s or $R_4$s are $CH_2$—$C_6H_5$), lysine (when the $R_3$s or $R_4$s $(CH_2)_4$—$NH_2$); or methionine (when the $R_3$s or $R_4$s are —$(CH_2)_2S(CH_3)$, and mixtures thereof.

The polyesteramide co-polymers preferably have an average number molecular weight (Mn) ranging from 15,000 to 200,000 Daltons. The polyesteramide co-polymers described herein can be fabricated in a variety of molecular weights and a variety of relative proportions of the m, p, and q units in the backbone. The appropriate molecular weight for a particular use is readily determined by one skilled in the art. A suitable Mn will be in the order of about 15,000 to about 100,000 Daltons, for example from about 30,000 to about 80,000 or from about 35,000 to about 75,000. Mn is measured via GPC in THF with polystyrene as standard.

The basic polymerization process of polyesteramides is based on the process described by G. Tsitlanadze, et al. J. Biomater. Sci. Polym. Edn. (2004) 15:1-24, however different building blocks and activating groups were used.

The polyesteramides of the present invention are for example synthesized as shown in scheme 1; via solution polycondensation of para-toluene sulfonate di-amines salts (X1, X2, X3) with activated di-acids (Y1). Typically dimethylsulfoxide or dimethylformamide are used as solvent. Typically as a base triethylamide is added, the reaction is carried out under an inert atmosphere at 60° C. for 24-72 hours under constant stirring. Subsequently the obtained reaction mixture is purified via a water precipitation followed by an organic precipitation and filtration. Drying under reduced pressure yields the polyesteramide.

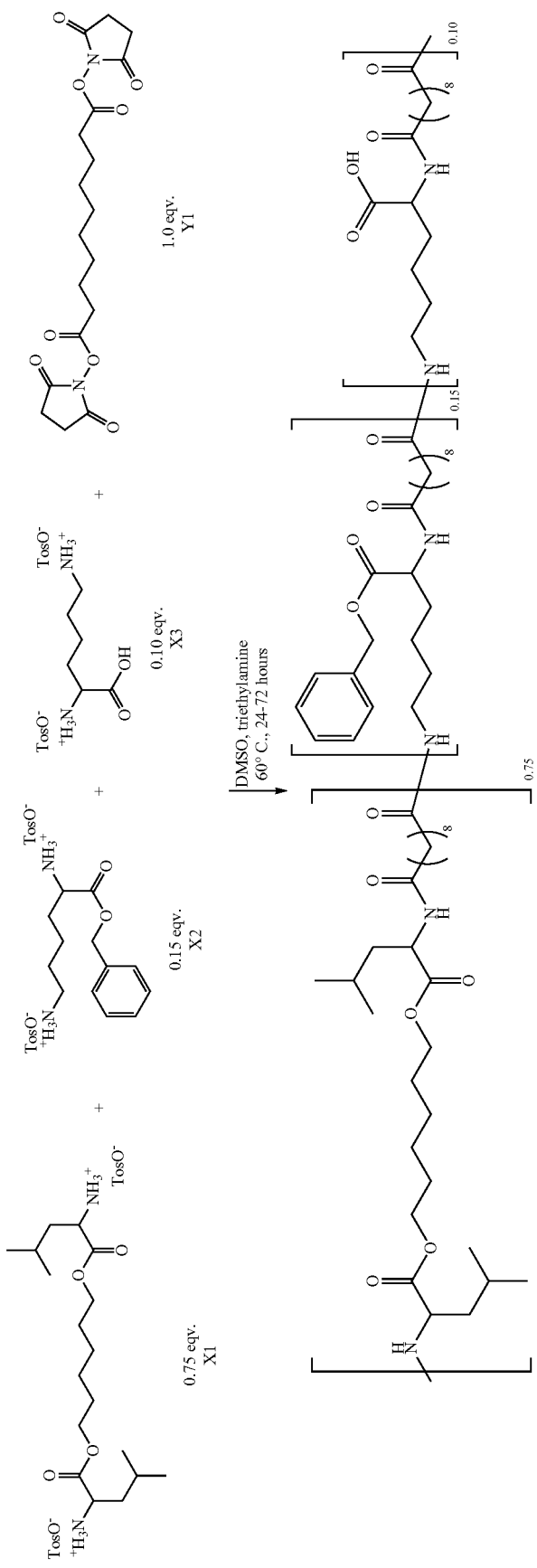
Scheme 1: schematic representation of PEA polymerization process, including some typical monomers.

The polyesteramide copolymers of the present invention may further comprise at least a bioactive agent. The bioactive agent can be any agent which is a therapeutic, prophylactic, or diagnostic agent. Such bioactive agent may include without any limitation small molecule drugs, peptides, proteins, DNA, cDNA, RNA, sugars, lipids and whole cells. The bioactive agents can have antiproliferative or anti-inflammatory properties or can have other properties such as antineoplastic, antiplatelet, anti-coagulant, anti-fibrin, antithrombotic, antimitotic, antibiotic, antiallergic, or antioxidant properties. Examples of antiproliferative agents include rapamycin and its functional or structural derivatives, 40-O-(2-hydroxy)ethyl-rapamycin (everolimus), and its functional or structural derivatives, paclitaxel and its functional and structural derivatives. Examples of rapamycin derivatives include ABT-578, 40-0-(3-hydroxy)propyl-rapamycin, 40-O-[2-(2-hydroxy)ethoxy]ethyl-rapamycin, and 40-0-tetrazole-rapamycin. Examples of paclitaxel derivatives include docetaxel. Examples of antineoplastics and/or antimitotics include methotrexate, azathioprine, vincristine, vinblastine, fluorouracil, doxorubicin hydrochloride (e.g. Adriamycin® from Pharmacia AND Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein Hb/nia platelet membrane receptor antagonist antibody, recombinant hirudin, thrombin inhibitors such as Angiomax (Biogen, Inc., Cambridge, Mass.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck AND Co., Inc., Whitehouse Station, N.J), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), super oxide dismutases, super oxide dismutase mimetic, 4-amino-2,2,6,6-tetramethylpiperidine-1-oxyl (4-amino-TEMPO), estradiol, anticancer agents, dietary supplements such as various vitamins, and a combination thereof. Examples of anti-inflammatory agents including steroidal and nonsteroidal anti-inflammatory agents include biolimus, tacrolimus, dexamethasone, clobetasol, corticosteroids or angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck AND Co., Inc., Whitehouse Station, N.J.). An example of an antiallergic agent is permirolast potassium. Other therapeutic substances or agents which may be appropriate include alpha-interferon, pimecrolimus, imatinib mesylate, midostaurin, and genetically engineered epithelial cells. The foregoing substances can also be used in the form of prodrugs or co-drugs thereof. The foregoing substances also include metabolites thereof and/or prodrugs of the metabolites. The foregoing substances are listed by way of example and are not meant to be limiting.

The present invention further relates to compositions comprising the polyesteramides according to the present. The polyesteramides may for example be blended with another polymer for example with a biocompatible polymer. The biocompatible polymer can be biodegradable or non-degradable. Examples of biocompatible polymers are ethylene vinyl alcohol copolymer, poly(hydroxyvalerate), polycaprolactone, poly(lactide-co-glycolide), poly(hydroxybutyrate), poly(hydroxybutyrate-co-valerate), polydioxanone, poly(glycolic acid-co-trimethylene carbonate), polyphosphoester urethane, poly(amino acids), polycyanoacrylates, poly(trimethylene carbonate), poly(iminocarbonate), polyurethanes, silicones, polyesters, polyolefins, polyisobutylene and ethylene-alphaolefin copolymers, acrylic polymers and copolymers, vinyl halide polymers and copolymers, such as polyvinyl chloride, polyvinyl ethers, such as polyvinyl methyl ether, polyvinylidene halides, polyvinylidene chloride, polyacrylonitrile, polyvinyl ketones, polyvinyl aromatics such as polystyrene, polyvinyl esters such as polyvinyl acetate, copolymers of vinyl monomers with each other and olefins, such as ethylene-methyl methacrylate copolymers, and ethylene-vinyl acetate copolymers, polyamides, such as Nylon 66 and polycaprolactam, alkyd resins, polycarbonates, polyoxymethylenes, polyimides, polyethers, poly(glyceryl sebacate), poly(propylene fumarate), epoxy resins, cellulose acetate, cellulose butyrate, cellulose acetate butyrate, cellophane, cellulose nitrate, cellulose propionate, cellulose ethers, and carboxymethyl cellulose, copolymers of these polymers with poly(ethylene glycol) (PEG), or combinations thereof.

In a preferred embodiments, the biocompatible polymer can be poly(ortho esters), poly(anhydrides), poly(D,L-lactic acid), poly (L-lactic acid), poly(glycolic acid), copolymers of poly(lactic) and glycolic acid, poly(L-lactide), glycolide), poly(phospho esters), poly(trimethylene carbonate), poly(oxa-esters), poly(oxa-amides), poly(ethylene carbonate), poly(propylene carbonate), poly(phosphoesters), poly(phosphazenes), poly(tyrosine derived carbonates), poly(tyrosine derived arylates), poly(tyrosine derived iminocarbonates), copolymers of these polymers with poly(ethylene glycol) (PEG), or combinations thereof. It is of course also possible that more than one polyesteramides of formula (IV) is mixed together or that the polyesteramides of the present invention are blended with other polyesteramides such as for example the disclosed prior art polyesteramides of Formula I or Formula II.

The polyesteramides may also comprise further excipients such as for example fillers, anti-oxidants, stabilizers, anti-caking agents, emulsifiers, foaming agents, sequestrants or dyes.

The polyesteramide copolymers of the present invention can be used in the medical field especially in drug delivery in the field of management of pain, musculoskeletal applications (MSK), ophthalmology, oncology, vaccine delivery compositions, dermatology, cardiovascular field, orthopedics, spinal, intestinal, pulmonary, nasal, or auricular.

The present invention further relates to articles comprising the polyesteramide copolymers of the present invention. In another aspect, the invention provides for a device comprising the polyesteramide copolymers of the present invention. In the context of the present invention an article is an individual object or item or element of a class designed to serve a purpose or perform a special function and can stand alone. Examples of articles include but are not limited to micro- and nanoparticles, coatings, films or micelles.

In yet another preferred embodiment, the invention provides for a device comprising the article of the present invention. A device is a piece of equipment or a mechanism designed to serve a special purpose or perform a special function and can consist of more than one article (multi-article assembly).

Examples of devices include, but are not limited to catheters, stents, rods, implants.

In another preferred embodiment, the invention provides for a polyesteramide copolymer of the present invention for use as a medicament.

The present invention will now be described in detail with reference to the following non limiting examples which are by way of illustration only.

Figure 1:
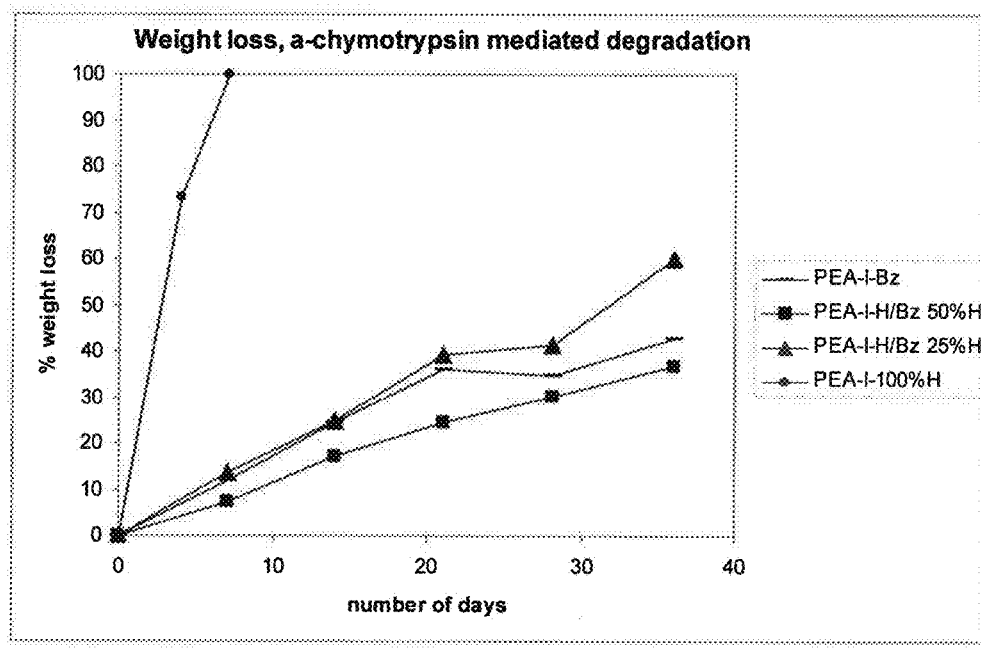
FIG. 1: The PEA weight loss after immersion in a buffer with 8.5 U/mL α-chymotrypsin is illustrated up to 36 days. The degradation of both PEA-I-H/Bz polymers follows closely the degradation of PEA-I-Bz., contrary to pure PEA-I-100% H which degraded much faster.

Example 1: (FIG. 1) (Degradation)

PEA-I-Bz, PEA-I-H/Bz 25% H, PEA-I-H/Bz 50% H and PEA-I-100% H were coated on stainless steel films and immersed in a buffer which contained 8.5 U/mL α-chymotrypsin (bovine) and 0.05% $NaN_3$, the buffers were refreshed twice a week. Weight loss over time was determined on dried samples using a micro balance. Results are given in FIG. 1.

It was observed that PEA-I-Bz, PEA-I-H/Bz 25% H and PEA-I-H/Bz 50% H degraded with a comparable degradation rate and lost 40-60% of the initial mass over the test period of 35 days. In contrast hereto PEA-I-100% H degraded much faster and degraded completely within 10 days.

Figure 2:
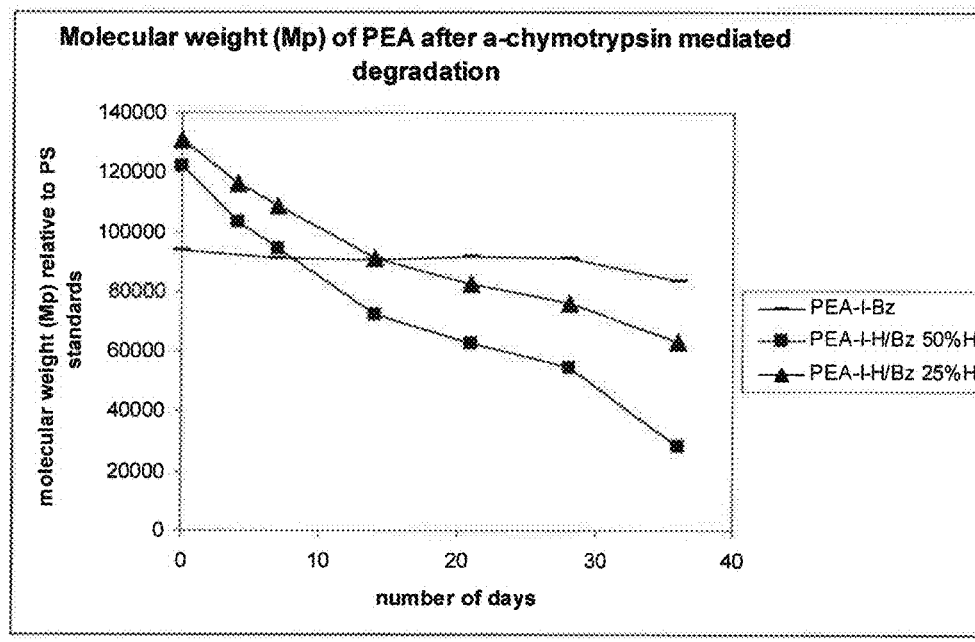
FIG. 2: The relative molecular weight of samples immersed in a solution which contained 8.5 U/mL α-chymotrypsin is illustrated up to 36 days. The relative molecular weight of PEA-I-Bz showed a marginal change while polymers with an increasing H % showed a clear molecular weight drop. Illustrating that also random chain scission (hydrolytic degradation) occurs for polymers which contain an increasing H %.

Example 2: (FIG. 2) (Mass Gain)

PEA-I-Bz, PEA-I-H/Bz 25% H and PEA-I-H/Bz 50% H were coated on stainless steel films and immersed in a buffer which contained 8.5 U/mL α-chymotrypsin (bovine) and 0.05% $NaN_3$, the buffers were refreshed twice a week. Relative molecular weights were evaluated with a GPC system using THF as the mobile phase on dried samples. Molecular weights are relative to polystyrene standards. Results are given in FIG. 2.

It was observed that PEA-I-Bz maintained a constant molecular weight. In contrast hereto PEA-I-H/Bz 25% H and PEA-I-H/Bz 50% H showed a significant drop in the molecular weight which indicates hydrolytic degradation of the bulk polymers.

Since the polymers also lost mass as illustrated in example 1 it was concluded that PEA-I-Bz degraded via surface erosion mediated by α-chymotrypsin. However since the molecular weight of PEA-I-H/Bz 25% H and PEA-I-H/Bz 50% H also dropped significantly it was concluded that these materials degrade via a combined degradation mechanism, both hydrolytic bulk degradation as well as enzymatic surface erosion.

Figure 3:
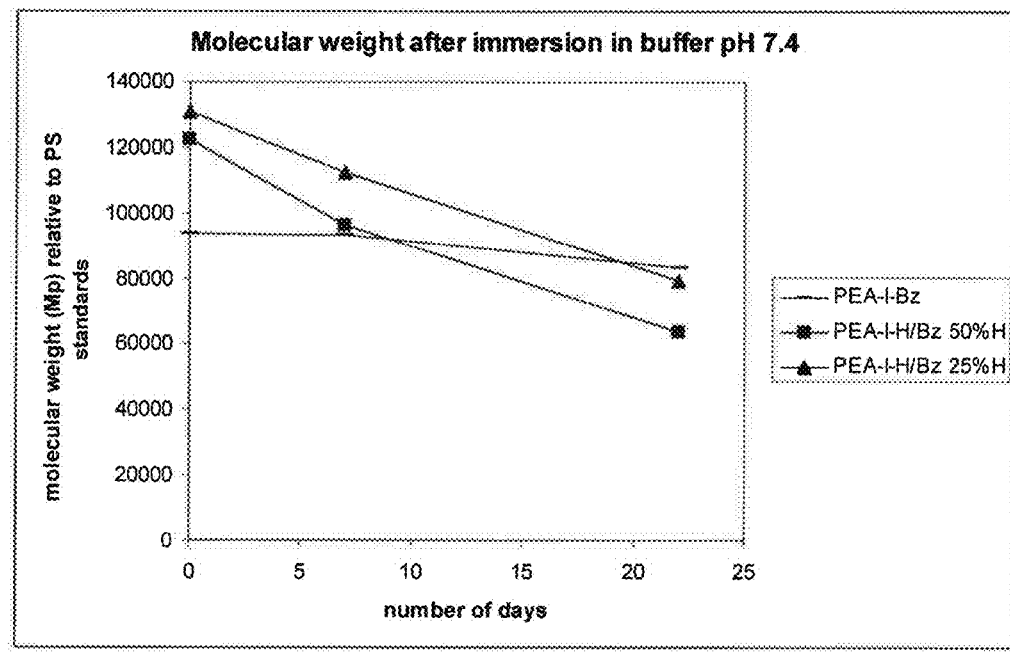
FIG. 3: The relative molecular weight evaluation of samples which were immersed in a buffer at pH 7.4 is illustrated up to 22 days. The relative molecular weight of PEA-I-Bz changed marginal while the molecular weights of polymers with an increasing H % showed a clear drop. Illustrating that random chain scission (hydrolytic degradation) occurs for polymers which contain an increasing H %.

Example 3 (FIG. 3) (Mass Gain)

PEA-I-Bz, PEA-I-H/Bz 25% H and PEA-I-H/Bz 50% H were coated on stainless steel films and immersed in a PBS buffer which contained 0.05% $NaN_3$; the buffers were refreshed twice a week. Relative molecular weights were evaluated with a GPC system using THF as the solvent on dried samples. Molecular weights are relative to polystyrene standards. Results are given in FIG. 3.

The graph illustrates that the molecular weight of PEA-I-Bz remained constant over the test period of 35 days indicating good hydrolytic stability of the material. In contrast the molecular weight of PEA-I-H/Bz 25% H and PEA-I-H/Bz 50% H films dropped significantly over the same period of time, indicating hydrolytic degradation of the materials. This example confirms that that the PEA-I-H/Bz polymers are indeed hydrolytically unstable and show hydrolytic bulk degradation.

Example 4 (FIGS. 4 and 5) Swelling/Mass Gain

From each PEA-I-H/Bz copolymer (5-, 25-, 50-, 100% H) five disks with a diameter of 10 mm were punched out of the film, weighed and placed in a 5.0 ml phosphate buffered saline (PBS) at 37° C. At several time intervals the disks were weighed to determine mass increase by water absorption. After each 2 days the PBS solution was refreshed. Results are given in FIGS. 4 and 5.

In FIG. 4, it was surprisingly found that PEA-I-H/Bz 5% H, PEA-I-H/Bz 25% H, PEA-I-H/Bz 35% H and PEA-I-H/Bz 50% H behaves very similar to PEA-I-Bz as shown in FIG. 4.

Figure 5:
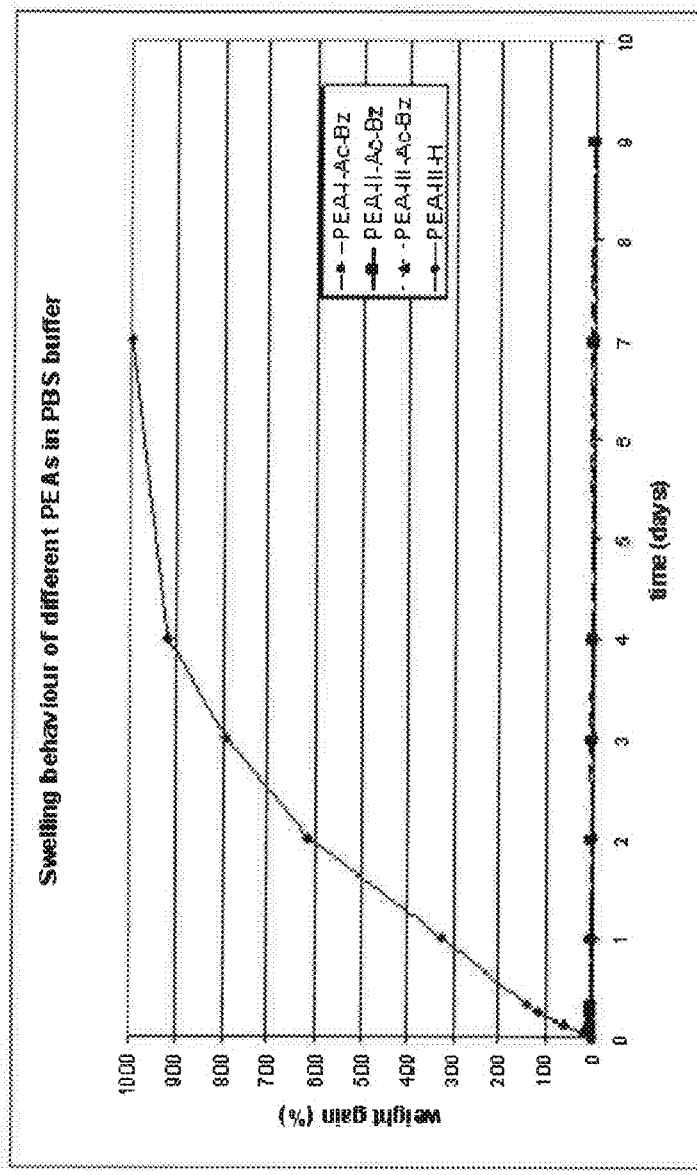
FIG. 5: Swelling behavior of different PEA's in PBS buffer.

In FIG. 5 it was observed that PEA-III-H exhibited a very fast swelling/water uptake, the material doubled in mass within the first hours after immersion in PBS buffer.

This was not the case for the remaining PEA-I-Bz and PEA-III-Bz polymers.

Example 5 (FIG. 6) Chloramphenicol Release

Drug loaded disks of PEA-I-Bz, PEA-I-H/Bz 25% H, PEA-I-H/Bz 50% H with a loading percentage of 10% chloroamphenicol were prepared. Three individual disks with a diameter of 7 mm were placed in 5.0 ml PBS buffer solution at 37° C. At varying time points the complete PBS solution was refreshed to assure sink conditions and the drug concentration was subsequently measured. Typically, samples were measured every day in the first week and weekly at later time points. Results are given in FIG. 6. Chloramphenicol release was measured by RP-HPLC on a C18 column with detection at 278 nm. The release of chloramphenicol from 10% loaded disks of PEA-I-H/Bz 25% H was faster compared to PEA-I-Bz.

FIG. 6 clearly shows that PEA-I-H/Bz 50% H disks do release chloramphenicol over period of 30 days, just slightly faster than PEA-I-Bz. Even more surprising PEA-I-H/Bz 25% H disks do provide even more sustained release of chloramphenicol than PEA-I-Bz.

Figure 7:
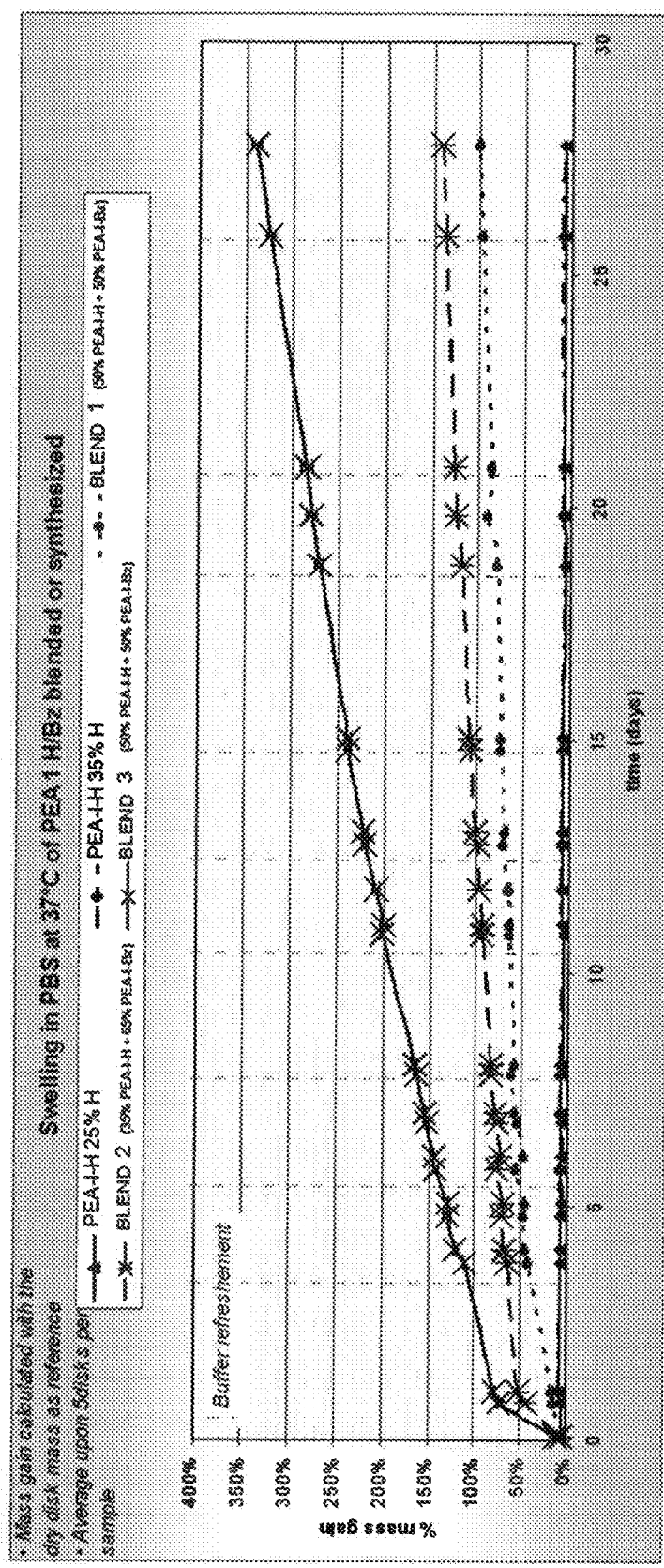
FIG. 7: Swelling properties of PEA-I-H/Bz (25% H and 35% H) compared to blends of PEA-H and PEA-Bz. Blend 1 comprising 25 wt % PEA-I-H and 75 wt % PEA-I-Bz; blend 2 comprising 35 wt % PEA-I-H and 65 wt % PEA-I-Bz; blend 3 comprising 50 wt % PEA-I-H and 50 wt % PEA-I-Bz.

Example 6 (FIG. 7 Blends Compared to PEA-I H/Bz)

The swelling behavior of polymers PEA-I-H/Bz 25% H, PEA-I-H 35% H and mechanical blends of PEA-I-H and PEA-I-Bz were compared; blend 1 comprises 25 wt % PEA-I-H and 75 wt % PEA I Bz, blend 2 comprises 35 wt % PEA-I-H and 65 wt % PEA I Bz and blend 3 comprises 50 wt % PEA-I-H and 50 wt % PEA I Bz. The polymers were dissolved in absolute ethanol to have approximately 20 g of solution at 10% (w/w) polymer. The dissolution took few hours. After that, the solution was poured in a Teflon dish (disk of 8 cm diameter). These disks were covered by a glass beaker or placed in a desiccator under nitrogen flow. When the surface was not sticky anymore, the disks were further dried under full vacuum at 65° C. The maximum vacuum was reached slowly to prevent from air bubbles formation. The temperature started to increase once the maximum vacuum was reached.

Five disks of 5 mm diameter were punched out of the 8 mm disks. They were weighted and placed in a 10 mL glass vial. Each disk was immersed in 5.0 mL of PBS buffer which was refreshed every 2 days. All the samples were kept at 37° C. For each data point, the disks were dried with a tissue and weighted. A data point was taken twice a day for the first three weeks, then once a day, then twice a week. The mass gain at time t was calculated with below Formula V;

$$\% \text{ mass gain} = \frac{\text{Dry disk mass} - \text{Disk mass at time } t}{\text{Dry disk mass}} \quad \text{Formula V}$$

Results are given in FIG. 7.

Example 8 (FIG. 8 Hydrolytic Degradation)

10 wt % solutions of PEA-I-Bz, PEA-I-H/Bz 5% H, PEA-I-H/Bz 15% H and PEA-I-35% H were prepared in ethanol. The polymer solutions were solvent casted on stainless steel foil with a thickness of 75 μm and dried under reduced pressure at 65° C. The obtained coated metal films were cut into pieces with a surface area of approximately 1 cm2. The polymer coated metal pieces were used to assess the polymer degradation over time. The polymer coated stainless steel pieces were individually immersed in 5 ml PBS buffer that contained 0.05% NaN3. In triplicate samples were taken and dried under reduced pressure at 65° C. The dried coatings were assessed via mass loss and molecular weight analysis using a GPC system with THF as the eluent. PEA-I-Bz illustrated a good hydrolytic stability based on the stable molecular weight, the introduction of very limited number of carboxyl groups (as in PEA-I-H/Bz 5% H) already results in minor drop of the molecular weight over time but apparently too slow to result in feasible polymer degradation. Surprisingly PEA-I-H/Bz 15% H and PEA-I-H/Bz 35% H showed a pronounced drop in the molecular weight associated with hydrolytic degradation of the polymers. Results are given in FIG. 8.

Example 9 (FIG. 9 Release Fluoresceine)

a. Preparation of the Solution of Polymers & Drugs and Film Preparation

A drug polymer formulation of 5 w % drug in polymer was prepared as followed. Approximately 100 mg of fluorescine were dissolved in 10 ml THF. After complete dissolution, the solution was used to dissolve ~2.0 g of polymer. Once a clear solution was obtained it was degassed by means of ultrasound the samples at least for 90 min. Afterwards, the solution was casted into a Teflon mould (Diameter=0.40 mm Depth=4 mm) up to full level. The solvent was allowed to evaporate at room temperature on air overnight. Then the whole Teflon mould was transferred into a vacuum oven for continuous evaporation at room temperature under gradually reduced pressure until the entire solvent was removed.

b. Disc Preparation

After evaporation of solvent, coated films were punched to obtain circled discs (Ø7 mm). The weight and thickness of each punched disc was determined. The weight of a used disc was approximately 15 to 30 mg.

c. Release Experiment

The punched discs from the dye-polymer coatings were prepared in duplo for the release experiment. The discs were immersed in 9 ml of PBS in a glass vial, being gently shaken at constant 37° C. during the release period. PBS solution was refreshed twice every day at the beginning of the experiment. Then the time was reduced to once per day and afterwards to once every two days at the later stage. The content of fluorescine released into the buffer solution was determined by either HPLC or UV spectroscopy.

Results are shown in FIG. 9.

FIG. 9 shows that in contrast of the PEA I Bz and PEA III Bz which provide sustained release on fluorescine, PEA-I-H and PEA-III-H polymers do release the entire drug load in 24-48 hours. This is a consequence of the quick and significant swelling of the polymers.

The invention claimed is:

1. An article or device comprising a bioactive agent and a biodegradable polyesteramide copolymer (PEA) according to the following formula:

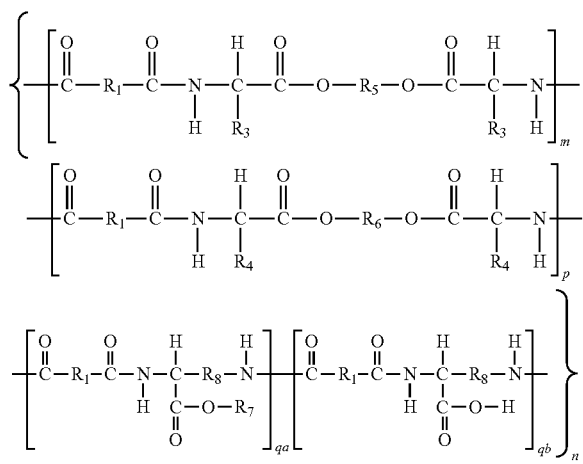

wherein
m+p is from 0.9-0.1 and q is from 0.1 to 0.9;
m+p+q=1 whereby one of m or p could be 0;
n is about 5 to about 300;
a is at least 0.05, b is at least 0.05, a+b=1, qa=q*a, and qb=q*b; wherein units of m (if present), units of p (if present), units of a, and units of b are all randomly distributed throughout the copolymer;
$R_1$ is independently selected from the group consisting of $(C_2-C_{20})$ alkylene, $(C_2-C_{20})$ alkenylene, —($R_9$—CO—O—$R_{10}$—O—CO—$R_9$)—, —$CHR_{11}$—O—CO—$R_{12}$—COOC$R_{11}$— and combinations thereof;
$R_3$ and $R_4$ in a single backbone unit m or p, respectively, are independently selected from the group consisting of hydrogen, $(C_1-C_6)$alkyl, $(C_2-C_6)$alkenyl, $(C_2-C_6)$alkynyl, $(C_6-C_{10})$aryl, $(C_1-C_6)$alkyl, —$(CH_2)SH$, —$(CH_2)_2S(CH_3)$, —$CH_2OH$, —CH(OH)CH$_3$, —$(CH_2)_4NH_3+$, —$(CH_2)_3NHC(=NH_2+)NH_2$, —$CH_2COOH$, —$(CH_2)COOH$, —$CH_2$—CO—NH$_2$, —$CH_2CH_2$—CO—NH$_2$, —$CH_2CH_2COOH$, $CH_3$—$CH_2$—$CH(CH_3)$—, $(CH_3)_2$—CH—CH$_2$—, H$_2$N—$(CH_2)_4$—, Ph-CH$_2$—, CH=C—CH$_2$—, HO-p-Ph-CH$_2$—, $(CH_3)_2$—CH—, Ph-NH—, NH—$(CH_2)_3$—C—, NH—CH=N—CH=C—CH$_2$—;
$R_5$ is selected from the group consisting of $(C_2-C_{20})$ alkylene, $(C_2-C_{20})$alkenylene, alkyloxy or oligoethyleneglycol;
$R_6$ is selected from bicyclic-fragments of 1,4:3,6-dianhydrohexitols of structural formula (III);

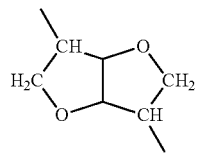

Formula III

R₇ is selected from the group consisting of $(C_6\text{-}C_{10})$ aryl $(C_1\text{-}C_6)$alkyl;

R₈ is —(CH₂)₄—;

R₉ or R₁₀ are independently selected from $C_2\text{-}C_{12}$ alkylene or $C_2\text{-}C_{12}$ alkenylene;

R₁₁ or R₁₂ are independently selected from H, methyl, $C_2\text{-}C_{12}$ alkylene or $C_2\text{-}C_{12}$ alkenylene.

2. The article or device according to claim 1, wherein a is at least 0.15.

3. The article or device according to claim 1, wherein a is at least 0.5.

4. The article or device according to claim 1, wherein a is at least 0.8.

5. The article or device according to claim 1, wherein p=0, m=0.75, and a=0.5;
wherein the m, qa, and qb units are randomly distributed;
R₁ is —(CH₂)₈—, R₃ is (CH₃)₂—CH—CH₂—, R₅ is hexyl, and R₇ is benzyl.

6. The article or device according to claim 1, wherein q=0.25, p=0.45, m=0.3, and a=0.5;
wherein the m, p, qa, and qb units are randomly distributed;
R₁ is —(CH₂)₈—; R₃ and R₄ respectively, are (CH₃)₂—CH—CH₂—; R₅ is $(C_2\text{-}C_{20})$alkylene; and R₇ is benzyl.

7. The article or device according to claim 1, wherein q=0.25, p=0.45, m=0.3, and a=0.75;
wherein the m, p, qa, and qb units are randomly distributed;
R₁ is —(CH₂)₈—; R₄ is (CH₃)₂—CH—CH₂—; and R₇ is benzyl.

8. The article or device according to claim 1, wherein q=0.1, p=0.30, m=0.6, and a=0.5;
wherein the m, p, qa, and qb units are randomly distributed;
R₁ —(CH₂)₄—; R₃ and R₄ respectively, are (CH₃)₂—CH—CH₂—; R₇ benzyl;
and R₅ is $(C_2\text{-}C_{20})$alkylene.

9. The article or device according to claim 1, wherein R₁ is independently selected from $(C_2\text{-}C_{20})$alkylene.

10. The article or device according to claim 1, wherein R₅ is $(C_2\text{-}C_{20})$alkylene.

11. The article or device according to claim 10, wherein R₅ is $(C_2\text{-}C_{20})$alkylene.

12. The article or device according to claim 1, wherein the biodegradable polyesteramide copolymer has an Mn of about 15,000 to about 100,000 Daltons, as measured via GPC in THF with polystyrene as standard.

13. The article or device according to claim 1, wherein the biodegradable polyesteramide copolymer has an Mn of about 30,000 to about 80,000 Daltons, as measured via GPC in THF with polystyrene as standard.

14. The article or device according to claim 11, wherein the biodegradable polyesteramide copolymer has an Mn of about 15,000 to about 100,000 Daltons, as measured via GPC in THF with polystyrene as standard.

15. The article or device according to claim 11, wherein the biodegradable polyesteramide copolymer has an Mn of about 30,000 to about 80,000 Daltons, as measured via GPC in THF with polystyrene as standard.

16. The article or device according to claim 7, wherein R₅ is $(C_2\text{-}C_{20})$alkylene.

17. The article or device according to claim 16, wherein the biodegradable polyesteramide copolymer has an Mn of about 15,000 to about 100,000 Daltons, as measured via GPC in THF with polystyrene as standard.

18. The article or device according to claim 16, wherein the biodegradable polyesteramide copolymer has an Mn of about 30,000 to about 80,000 Daltons, as measured via GPC in THF with polystyrene as standard.

19. The article or device according to claim 1, wherein the article or the device is a film, a coating, a micelle, a catheter, a stent, a rod, a microparticle, a nanoparticle, or an implant.

20. The article or device according to claim 2, wherein the article or the device is a film, a coating, a micelle, a catheter, a stent, a rod, a microparticle, a nanoparticle, or an implant.

21. The article or device according to claim 3, wherein the article or the device is a film, a coating, a micelle, a catheter, a stent, a rod, a microparticle, a nanoparticle, or an implant.

22. The article or device according to claim 11, wherein the article or the device is a film, a coating, a micelle, a catheter, a stent, a rod, a microparticle, a nanoparticle, or an implant.

23. The article or device according to claim 14, wherein the article or the device is a film, a coating, a micelle, a catheter, a stent, a rod, a microparticle, a nanoparticle, or an implant.

24. The article or device according to claim 15, wherein the article or the device is a film, a coating, a micelle, a catheter, a stent, a rod, a microparticle, a nanoparticle, or an implant.

25. The article or device according to claim 16, wherein the article or the device is a film, a coating, a micelle, a catheter, a stent, a rod, a microparticle, a nanoparticle, or an implant.

26. The article or device according to claim 17, wherein the article or the device is a film, a coating, a micelle, a catheter, a stent, a rod, a microparticle, a nanoparticle, or an implant.

27. The article or device according to claim 18, wherein the article or the device is a film, a coating, a micelle, a catheter, a stent, a rod, a microparticle, a nanoparticle, or an implant.

28. The article or device according to claim 1, wherein the article or device is a drug delivery device for ophthalmology applications and the bioactive agent is a small molecule ophthalmic drug, or prodrug or metabolite thereof.

29. The article or device according to claim 2, wherein the article or device is a drug delivery device for ophthalmology applications and the bioactive agent is a small molecule ophthalmic drug, or prodrug or metabolite thereof.

30. The article or device according to claim 3, wherein the article or device is a drug delivery device for ophthalmology applications and the bioactive agent is a small molecule ophthalmic drug, or prodrug or metabolite thereof.

31. The article or device according to claim 11, wherein the article or device is a drug delivery device for ophthalmology applications and the bioactive agent is a small molecule ophthalmic drug, or prodrug or metabolite thereof.

32. The article or device according to claim 14, wherein the article or device is a drug delivery device for ophthalmology applications and the bioactive agent is a small molecule ophthalmic drug, or prodrug or metabolite thereof.

33. The article or device according to claim 15, wherein the article or device is a drug delivery device for ophthalmology applications and the bioactive agent is a small molecule ophthalmic drug, or prodrug or metabolite thereof.

34. The article or device according to claim 16, wherein the article or device is a drug delivery device for ophthalmology applications and the bioactive agent is a small molecule ophthalmic drug, or prodrug or metabolite thereof.

35. The article or device according to claim 17, wherein the article or device is a drug delivery device for ophthalmology applications and the bioactive agent is a small molecule ophthalmic drug, or prodrug or metabolite thereof.

36. The article or device according to claim 18, wherein the article or device is a drug delivery device for ophthalmology applications and the bioactive agent is a small molecule ophthalmic drug, or prodrug or metabolite thereof.

* * * * *

UNITED STATES PATENT AND TRADEMARK OFFICE
CERTIFICATE OF CORRECTION

PATENT NO. : 9,873,765 B2  
APPLICATION NO. : 15/252350  
DATED : January 23, 2018  
INVENTOR(S) : Guy Draaisma and George Mihov Page 1 of 1

It is certified that error appears in the above-identified patent and that said Letters Patent is hereby corrected as shown below:

In the Specification

Column 5, Lines 8-9, please replace "$CH_2$-, $(CH_3)_2$-CH-, Ph-NH-, NH-$(CH_2)_3$-C-, NH-CH=N-CH=C-$CH_2$-." with the following:
$CH_2$-, $(CH_3)_2$-CH-, PH-NH-, NH-$(CH_2)_3$-C-, NH-CH=N-CH=C-$CH_2$-.

In the Claims

Column 16, Claim 1, Lines 51-52, please replace "Ph-NH-, NH=$(CH_2)_3$-C-, NH-CH=N-CH=C-$CH_2$-;" with the following:
Ph-NH-, NH-$(CH_2)_3$-C-, NH-CH=N-CH=C-$CH_2$-;

Signed and Sealed this  
Twenty-sixth Day of March, 2019

Andrei Iancu  
*Director of the United States Patent and Trademark Office*